United States Patent
Wang et al.

(10) Patent No.: US 10,444,311 B2
(45) Date of Patent: Oct. 15, 2019

(54) METHODS AND DEVICES FOR OPTIMIZING MAGNETIC RESONANCE IMAGING PROTOCOLS

(71) Applicants: OHIO STATE INNOVATION FOUNDATION, Columbus, OH (US); RESEARCH INSTITUTE AT NATIONWIDE CHILDREN'S HOSPITAL, Columbus, OH (US)

(72) Inventors: Jinghua Wang, Columbus, OH (US); Zhong-lin Lu, Dublin, OH (US); Nehal Parikh, Columbus, OH (US); Lili He, Columbus, OH (US)

(73) Assignees: Ohio State Innovation Foundation, Columbus, OH (US); Research Institute at Nationwide Children's Hospital, Columbus, OH (US)

( * ) Notice: Subject to any disclaimer, the term of this patent is extended or adjusted under 35 U.S.C. 154(b) by 100 days.

(21) Appl. No.: 15/557,120

(22) PCT Filed: Mar. 11, 2016

(86) PCT No.: PCT/US2016/022086
§ 371 (c)(1),
(2) Date: Sep. 10, 2017

(87) PCT Pub. No.: WO2016/145355
PCT Pub. Date: Sep. 15, 2016

(65) Prior Publication Data
US 2018/0045799 A1    Feb. 15, 2018

Related U.S. Application Data

(60) Provisional application No. 62/131,737, filed on Mar. 11, 2015.

(51) Int. Cl.
*G01R 33/48* (2006.01)
*G01R 33/54* (2006.01)
(Continued)

(52) U.S. Cl.
CPC .......... *G01R 33/4818* (2013.01); *A61B 5/004* (2013.01); *A61B 5/0042* (2013.01);
(Continued)

(58) Field of Classification Search
CPC .. G01R 33/4818; G01R 33/543; A61B 5/004; A61B 5/0042; A61B 5/055;
(Continued)

(56) References Cited

U.S. PATENT DOCUMENTS 4,707,658 A    11/1987   Frahm et al.
5,150,053 A     9/1992   Pauly et al.
(Continued)

OTHER PUBLICATIONS

International Search Report and Written Opinion, dated May 26, 2016 issued in corresponding PCT Application No. PCT/US2016/022086.
(Continued)

*Primary Examiner* — Rodney A Bonnette
(74) *Attorney, Agent, or Firm* — Meunier Carlin & Curfman LLC

(57) ABSTRACT

Techniques for optimizing a magnetic resonance imaging (MRI) protocols are described herein. An example method can include receiving one or more MRI scanner settings for an imaging sequence; selecting at least one objective function from a plurality of objective functions; selecting an acquisition train length; selecting a k-space strategy; selecting one or more imaging parameters; and acquiring a magnetic resonance (MR) image using at least one of an optimized k-space strategy, an optimized acquisition train length, or optimized imaging parameters.

34 Claims, 27 Drawing Sheets

(51) Int. Cl.
*A61B 5/00* (2006.01)
*A61B 5/055* (2006.01)

(52) U.S. Cl.
CPC ............ *A61B 5/055* (2013.01); *G01R 33/543* (2013.01); *A61B 2503/02* (2013.01); *A61B 2503/045* (2013.01); *A61B 2503/06* (2013.01); *A61B 2503/08* (2013.01); *A61B 2503/12* (2013.01); *A61B 2576/02* (2013.01); *A61B 2576/026* (2013.01)

(58) Field of Classification Search
CPC .......... A61B 2503/02; A61B 2503/045; A61B 2503/06; A61B 2503/08; A61B 2503/12; A61B 2576/02; A61B 2576/026
See application file for complete search history.

(56) References Cited

U.S. PATENT DOCUMENTS

| | | | |
|---|---|---|---|
| 5,245,282 | A | 9/1993 | Mugler, III et al. |
| 5,551,431 | A | 9/1996 | Wells, III et al. |
| 5,818,229 | A | 10/1998 | Kanazawa |
| 6,265,875 | B1 | 7/2001 | Saranathan et al. |
| 6,400,151 | B1 | 6/2002 | Haase et al. |
| 6,414,487 | B1 | 7/2002 | Anand et al. |
| 6,965,235 | B1 | 11/2005 | Guclu et al. |
| 7,078,899 | B2 | 7/2006 | Dale et al. |
| 7,489,962 | B2 | 2/2009 | Cull et al. |
| 7,515,951 | B2 | 4/2009 | Egan et al. |
| 7,705,597 | B2 | 4/2010 | Horger et al. |
| 7,715,899 | B2 | 5/2010 | Harvey et al. |
| 7,821,266 | B2 | 10/2010 | Feiweier |
| 8,159,222 | B2 | 4/2012 | King et al. |
| 8,319,495 | B1 | 11/2012 | Zhu |
| 8,874,189 | B2 | 10/2014 | Warntjes |
| 2003/0030435 | A1 | 2/2003 | Venkatesan et al. |
| 2007/0116695 | A1* | 5/2007 | Fallon ................. A61K 31/37 424/94.2 |
| 2007/0236216 | A1 | 10/2007 | Pipe |
| 2008/0129298 | A1 | 6/2008 | Vaughan et al. |
| 2008/0150532 | A1 | 6/2008 | Slavin et al. |
| 2010/0004909 | A1 | 1/2010 | Nitz |
| 2010/0127703 | A1 | 5/2010 | Sung et al. |
| 2010/0239151 | A1 | 9/2010 | Dannels et al. |
| 2012/0032676 | A1 | 2/2012 | Dannels |
| 2012/0314926 | A1* | 12/2012 | Ghosh ...................... G06K 9/38 382/131 |
| 2013/0038326 | A1 | 2/2013 | Amadon et al. |
| 2013/0335083 | A1 | 12/2013 | Wasserman et al. |
| 2014/0011217 | A1* | 1/2014 | Weissleder ....... G01N 33/57484 435/7.32 |
| 2014/0039300 | A1 | 2/2014 | Gjesdal et al. |
| 2015/0071514 | A1 | 3/2015 | Wang et al. |
| 2015/0196222 | A1 | 7/2015 | Stehning et al. |
| 2016/0113501 | A1 | 4/2016 | Hua et al. |

OTHER PUBLICATIONS

Bampton, et al., "Centric Phase-Encoding Order in Three-dimensional MP-RAGE Sequences: Application to Abdominal Imaging," Journal of Magnetic Resonance Imaging, vol. 2, No. 3, 1992, pp. 327-334.

Boulant, et al., "High tip angle approximation based on a modified Bloch-Riccati equation". Magn Reson Med. 2012;67(2):339-43.

Jurcoane, et al., "Within-lesion differences in quantitative MRI parameters predict contrast enhancement in multiple sclerosis", J Magn Reson Imaging 2013, 38(6): 1454-1461.

Kober, et al., "MP2RAGE multiple sclerosis magnetic resonance imaging at 3 T", Invest Radiol 2012,47(6): 346-352.

Lukzen, et al., "Analytical derivation of multiple spin echo amplitudes with arbitrary refocusing angle", J Magn Reson. 2007;185(1):71-6.

Murase, et al., "Numerical solutions to the time-dependent Bloch equations revisited", Magn Reson Imaging. 2011;29(1):126-31.

Tardif, et al., "Regional Impact of Field Strength on Voxel-Based Morphometry Results," Human Brain Mapping, vol. 31, 2010, pp. 943-957.

Wang, et al., "In Vivo Method for Correcting Transmit/Receive Nonuniformities with Phased Array Coils," Magnetic Resonance in Medicine, vol. 53, 2005, pp. 666-674.

Wang, et al., "Measurement and Correction of Transmitter and Receiver Induced Nonuniformities in Vivo," Magnetic Resonance in Medicine, vol. 53, 2005, pp. 408-417.

Williams, et al., "Optimization of 3D MP-RAGE for neonatal brain imaging at 3.0", Magnetic resonance imaging 2007; 25: 1162-70.

* cited by examiner

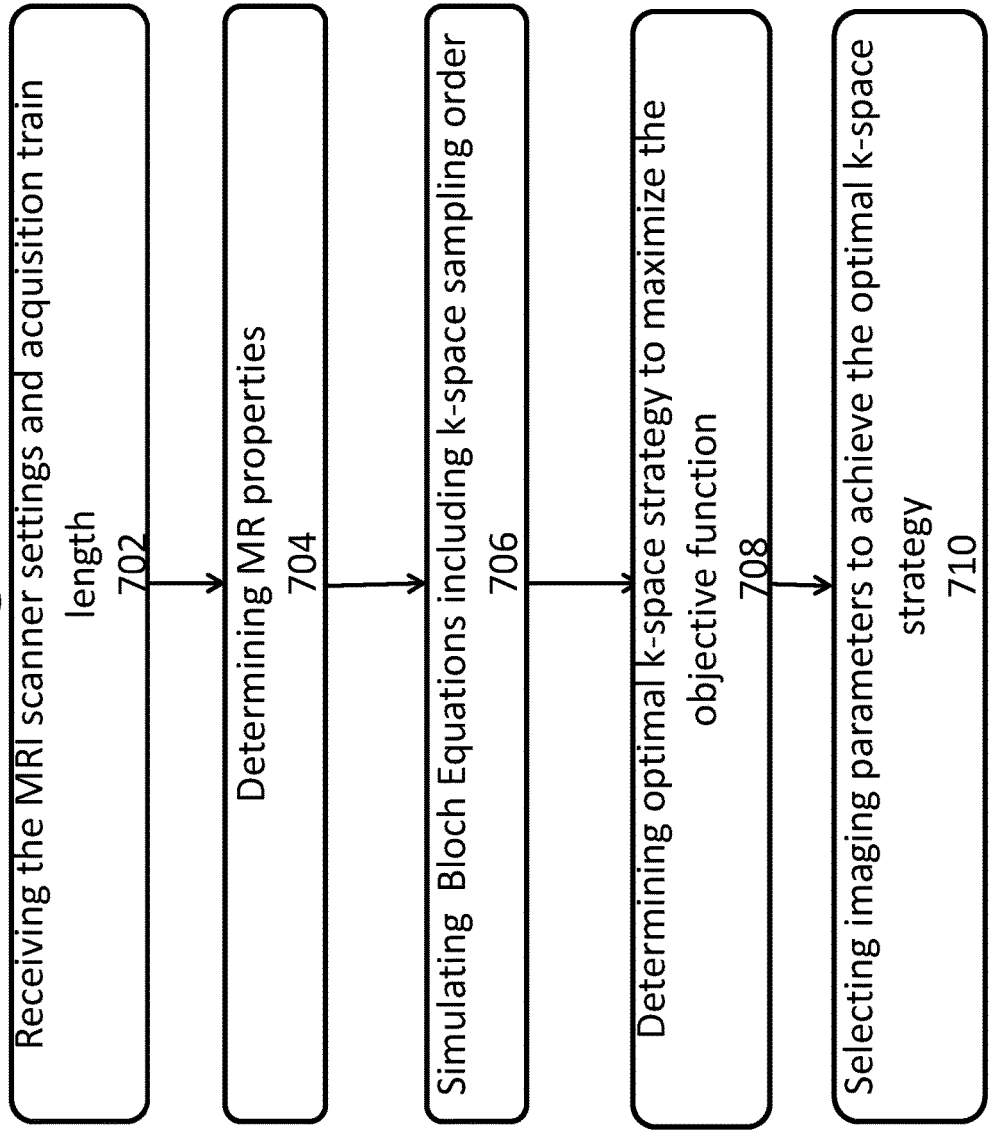

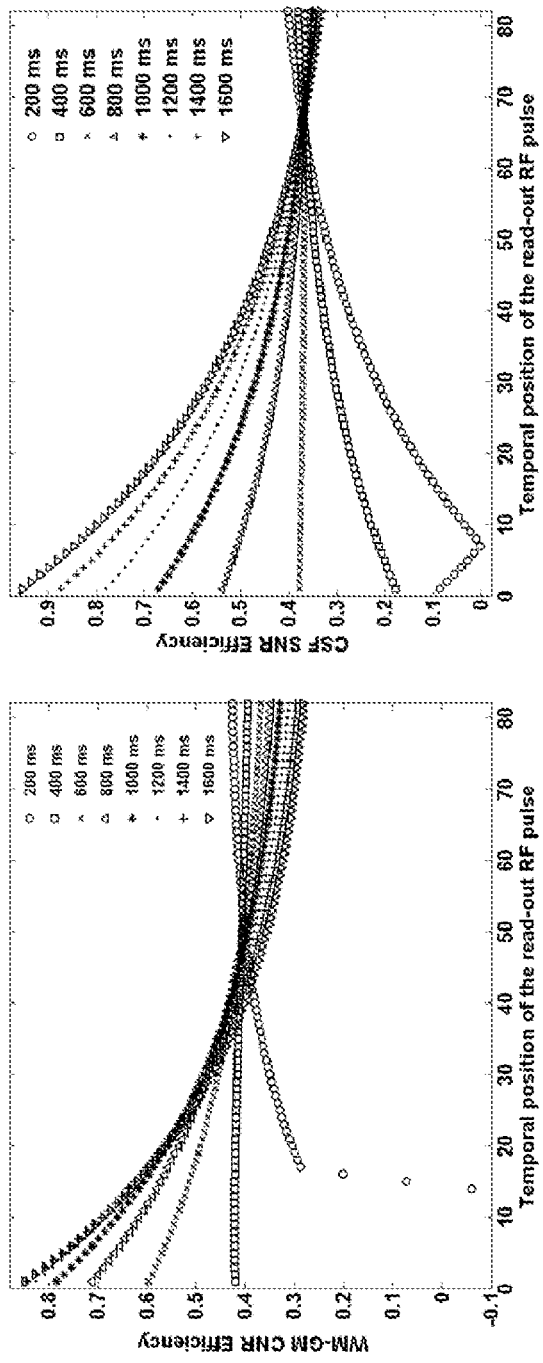

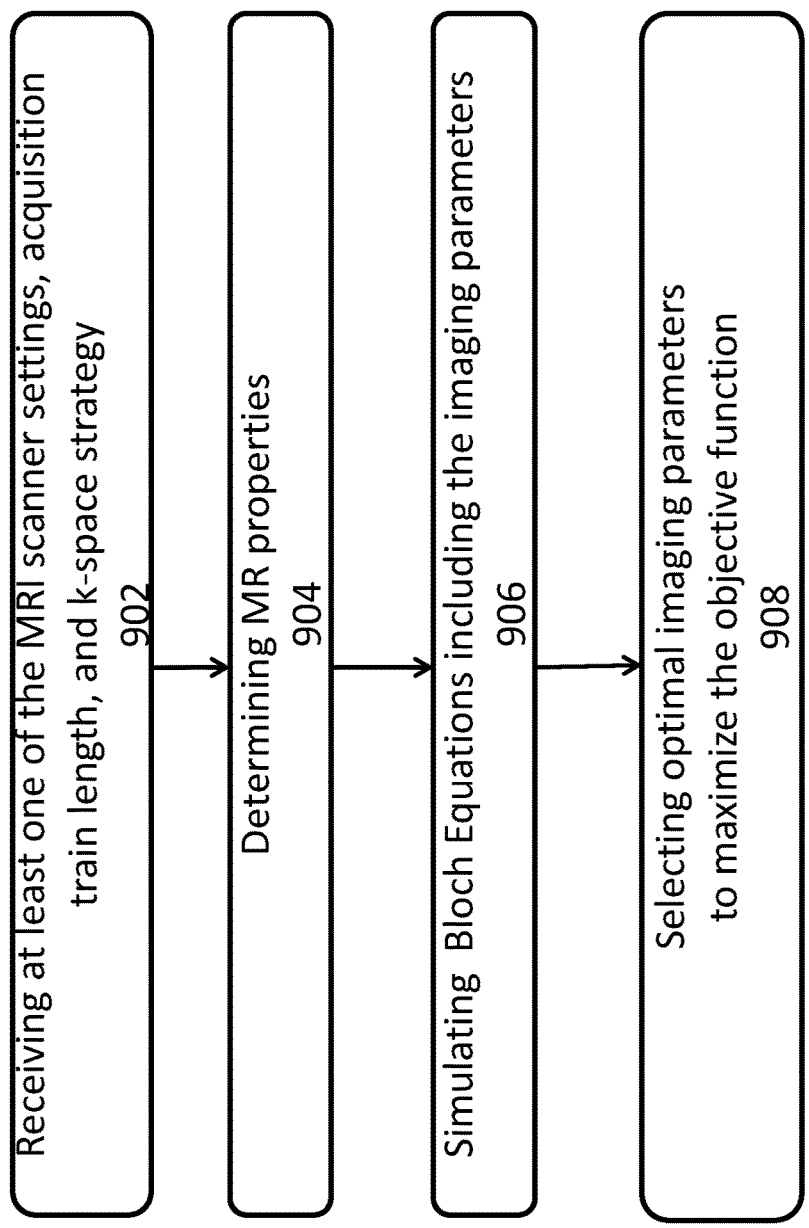

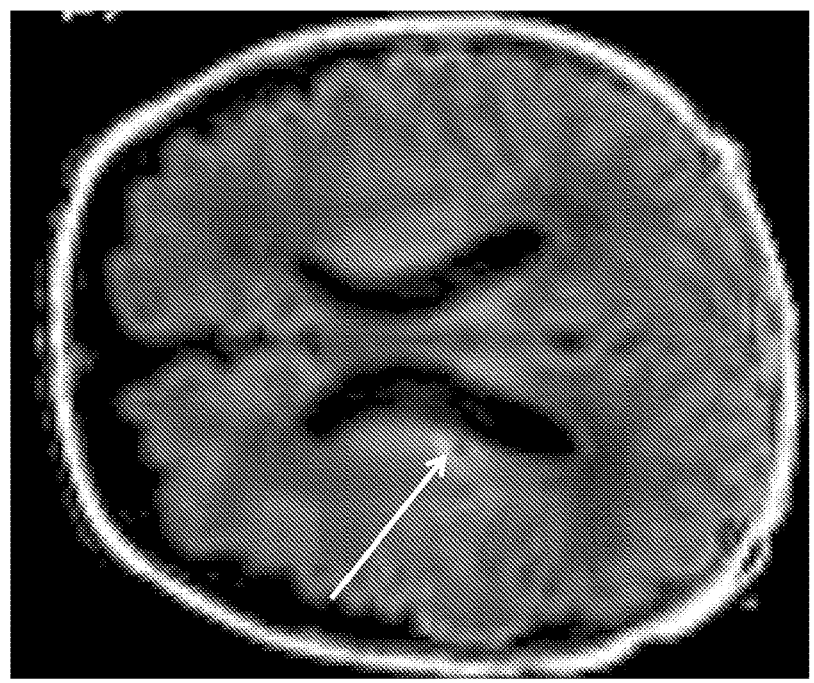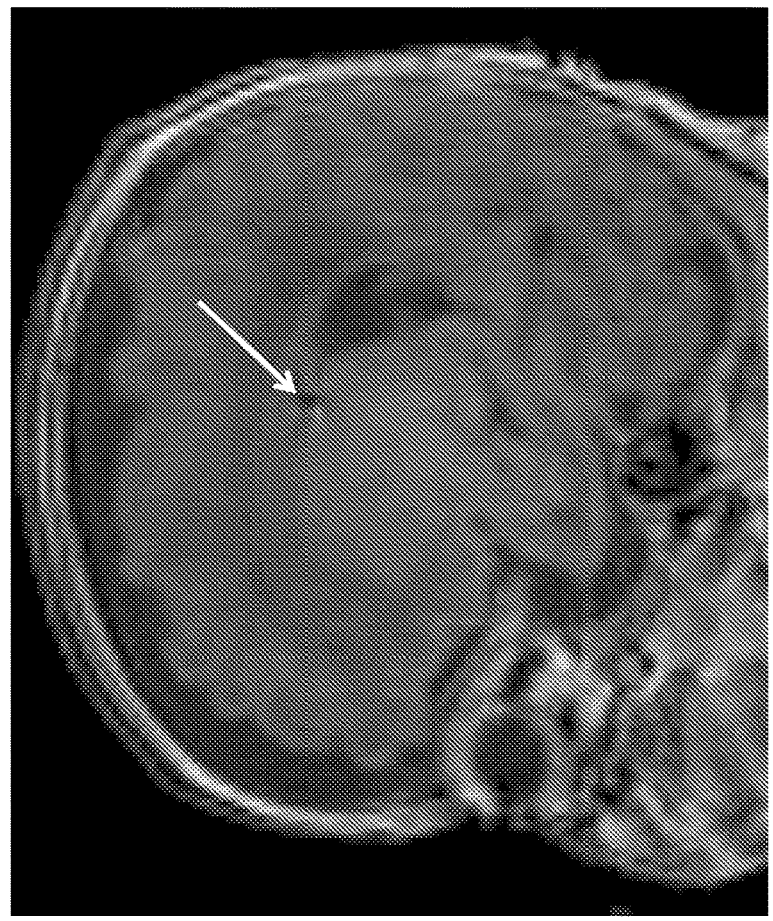
Figure 19

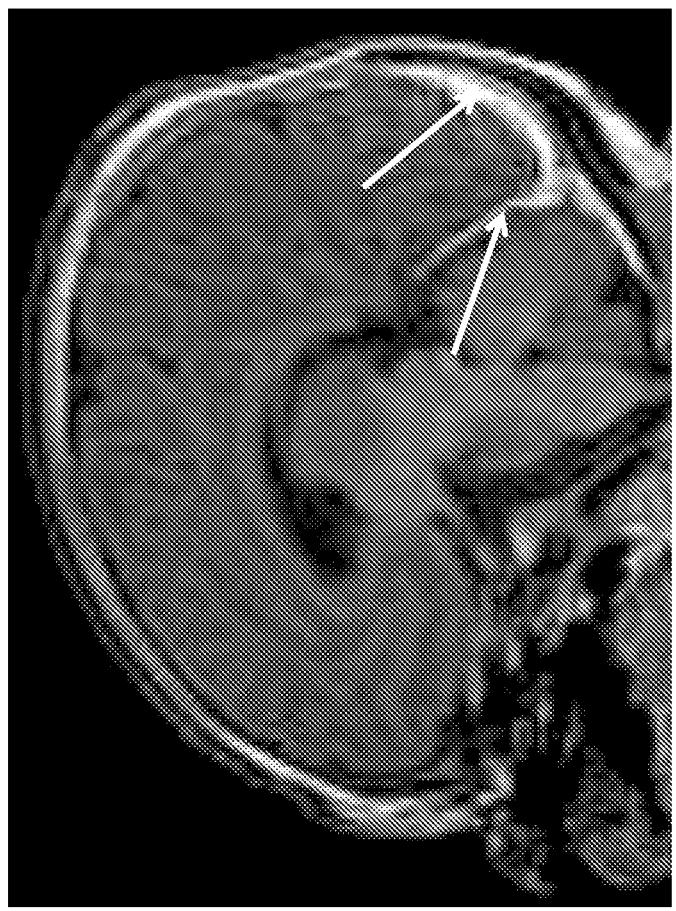
Figure 20

Figure 21
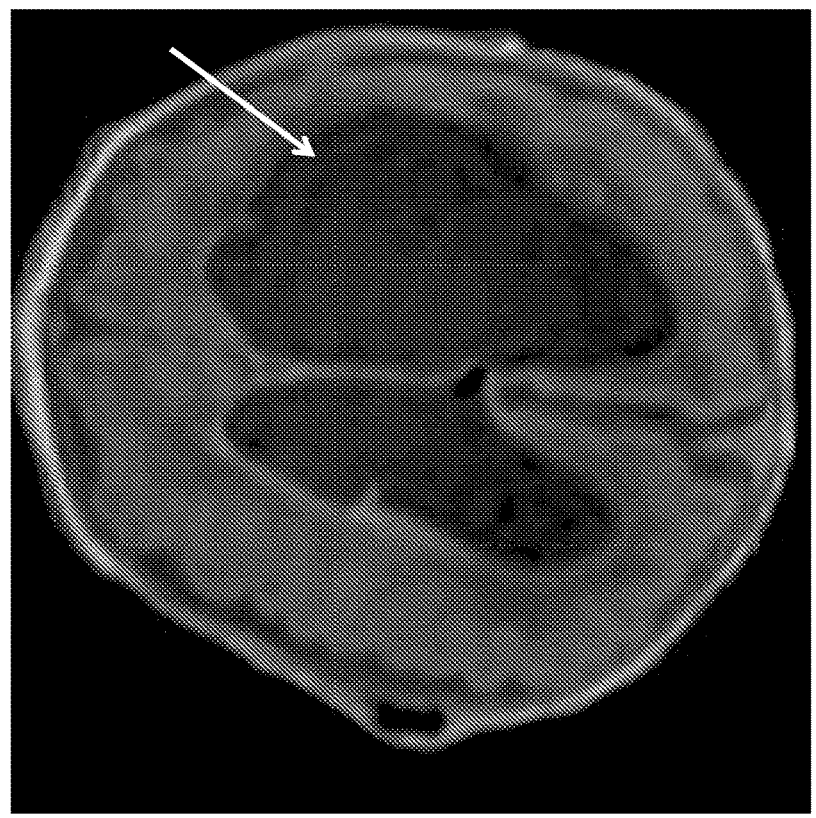
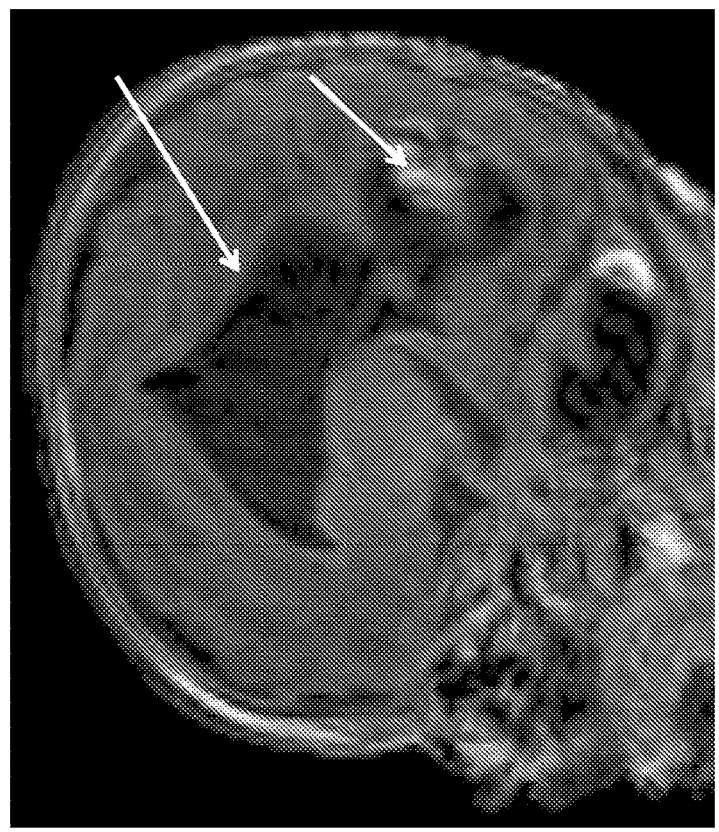

Figure 23
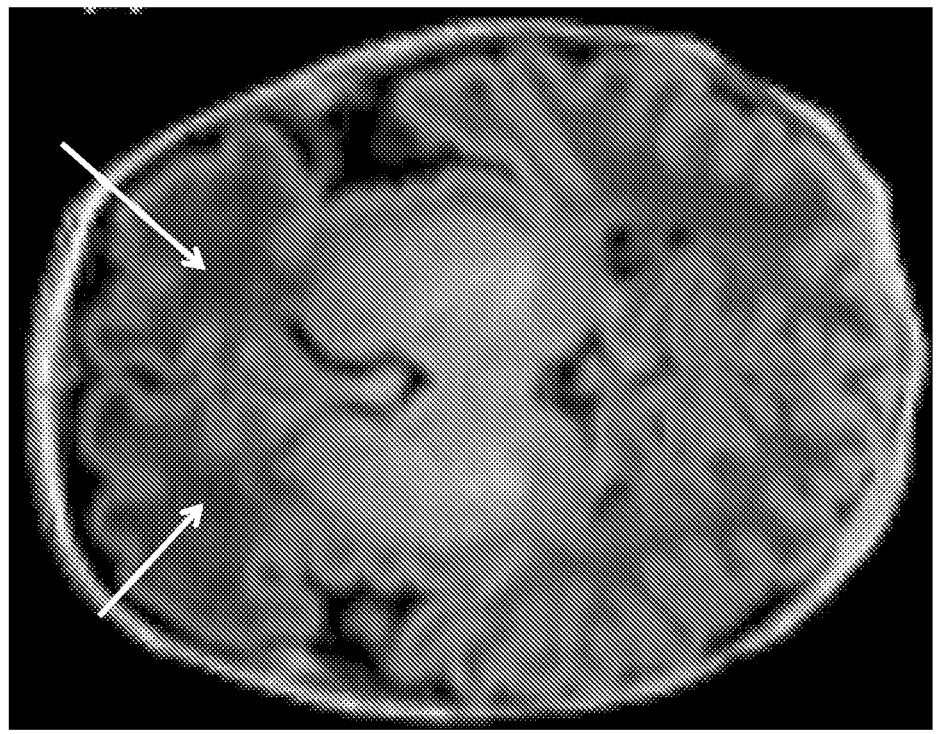
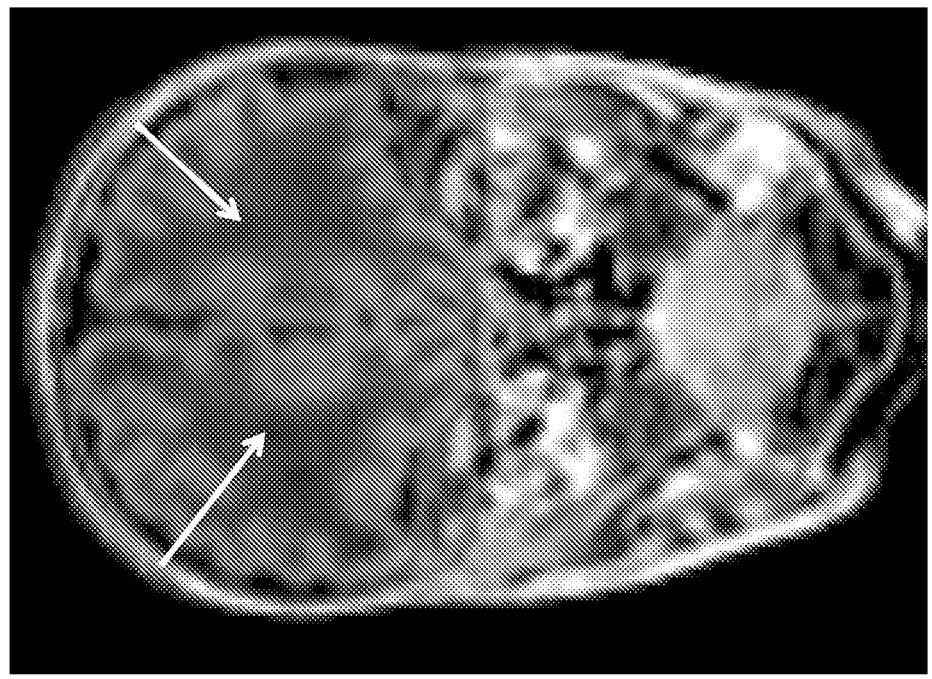

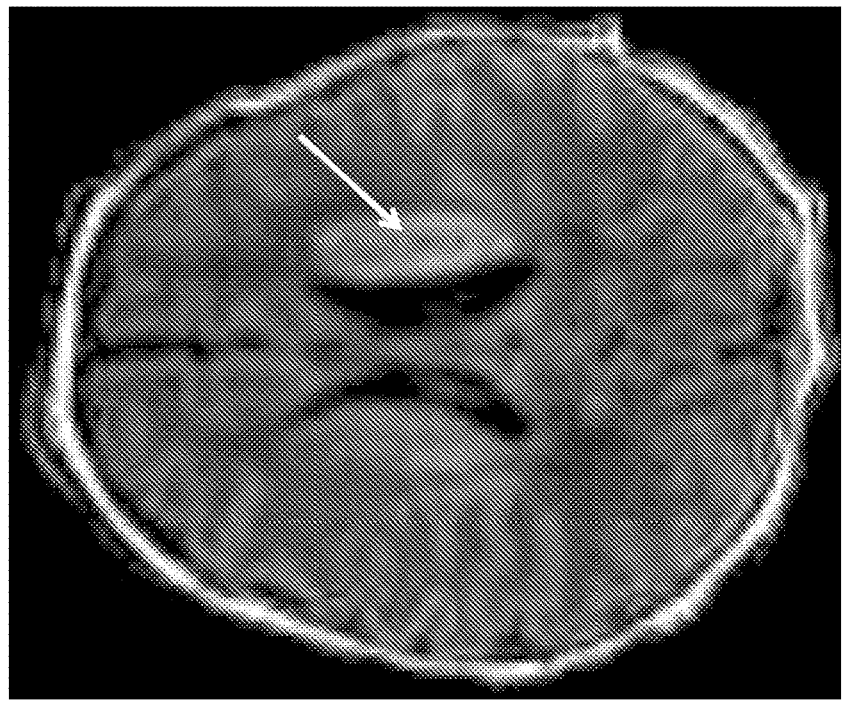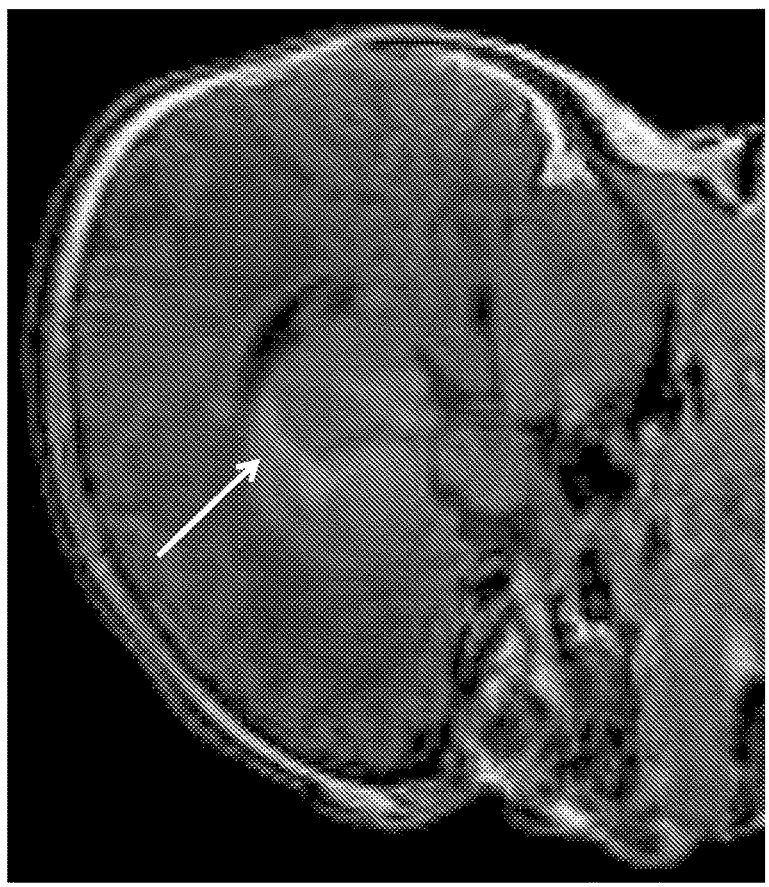
Figure 26

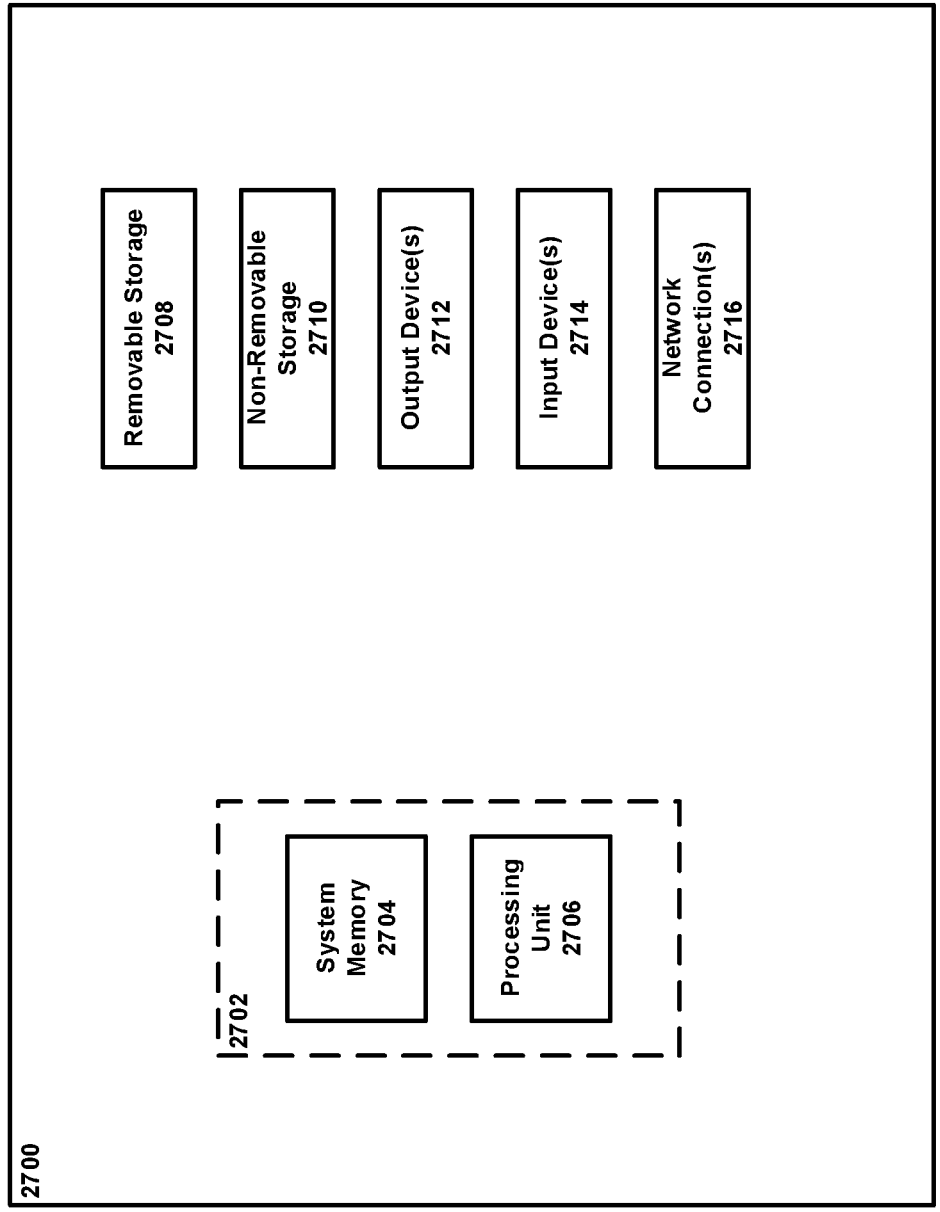

METHODS AND DEVICES FOR OPTIMIZING MAGNETIC RESONANCE IMAGING PROTOCOLS

CROSS-REFERENCE TO RELATED APPLICATIONS

This application is a national stage application filed under 35 U.S.C. § 371 of PCT/US2016/022086 filed Mar. 11, 2016, which claims the benefit of U.S. Provisional Patent Application No. 62/131,737, filed on Mar. 11, 2015, entitled "METHODS AND DEVICES FOR OPTIMIZING MAGNETIC RESONANCE IMAGING PROTOCOLS," the disclosure of which is expressly incorporated herein by reference in its entirety.

BACKGROUND

Magnetic Resonance Imaging (MRI) is one of the most important modern medical imaging modalities. It has far less risk of side effects than most other imaging modalities such as radioscopy with x-rays or computed tomography because patients and medical personnel are not subjected to ionizing radiation exposure in the procedure. The use of MRI has grown very fast. Every year, more than 30 million MRI scans are performed in the United States; more than 60 million MRI scans are performed worldwide. Doctors often recommend MRI for the diagnosis of various diseases, such as tumors, strokes, heart problems, and spine diseases. A high-quality scan is important for maximizing diagnostic sensitivity and accuracy. Generally, high quality images are characterized by high signal to noise ratio (SNR), high contrast between normal and pathological tissues, low levels of artifacts, and appropriate spatial-temporal resolution.

In order to obtain a detectable MR signal, the object/subject examined is positioned in a homogeneous static magnetic field so that the object's nuclear spins generate net magnetization oriented along the static magnetic field. The net magnetization is rotated away from the static magnetic field using a radio frequency (RF) excitation field with the same frequency as the Larmor frequency of the nucleus. The angle of rotation is determined by the field strength of the RF excitation pulse and its duration. In the end of the RF excitation pulse, the nuclei, in relaxing to their normal spin conditions, generate a decaying signal (the "MR signal") at the same radio frequency as the RF excitation. The MR signal is picked up by a receive coil, amplified and processed. The acquired measurements, which are collected in the spatial frequency domain, are digitized and stored as complex numerical values in a "k-space" matrix. An associated MR image can be reconstructed from the k-space data, for example, by an inverse 2D or 3D fast Fourier transformation (FFT) from the raw k-space data.

SUMMARY

An example method for optimizing a magnetic resonance imaging (MRI) protocol is described herein. The method can include receiving one or more MRI scanner settings for an imaging sequence; selecting at least one objective function from a plurality of objective functions; selecting an acquisition train length; selecting a k-space strategy based on the acquisition train length; optimizing one or more imaging parameters; and acquiring a magnetic resonance (MR) image using at least one of the k-space strategy, the acquisition train length, or the one or more imaging parameters.

Alternatively or additionally, selecting a k-space strategy can include optimizing k-space strategies. It should be understood that k-space strategy optimization is not available for sequences in which each respective k-space acquisition has the same objective function (e.g., image quality) as that used for k-space optimization. Examples of such sequences include spoiled or full relaxation gradient echo, or spin echo sequences. Additionally, it should be understood that k-space strategy optimization is available for acquisition train with and/or without magnetization preparation.

Alternatively or additionally, optimizing a k-space strategy can include receiving one or more MRI scanner settings and an acquisition train length; determining one or more magnetic resonance (MR) parameters of a region of interest; using the one or more MR parameters, simulating respective relationships among at least one objective function with the acquisition train length; and selecting the k-space strategy to optimize the at least one objective function. As described herein, the simulation can be performed using Bloch Equations (also referred to herein as Bloch's Equations). Additionally, a solution of the Bloch Equations can be at least one of an analytic solution, a numerical solution, or an approximation solution.

Alternatively or additionally, the k-space strategy can include a k-space trajectory and a sampling order. The k-space trajectory can include at least one of a rectilinear, radial, echo planar imaging, spiral, projection reconstruction, random, under-sampled, or partial k-space sampling trajectory. The sampling order can include at least one of a sequential, centric, interleaved, reverse, or random sampling order.

An example method for optimizing acquisition train length is described herein. The method can include receiving one or more magnetic resonance imaging (MRI) scanner settings for an imaging sequence; determining one or more magnetic resonance (MR) parameters of a region of interest; using the one or more MR parameters, simulating respective relationships among an acquisition train length and an objective function for the region of interest; optimizing the acquisition train length to maximize the objective function for the region of interest; and selecting one or more imaging parameters to achieve the optimal acquisition train length. As described herein, the simulation can be performed using Bloch Equations. Additionally, a solution of the Bloch Equations can be at least one of an analytic solution, a numerical solution, or an approximation solution.

Alternatively or additionally, the method for optimizing acquisition train length can further include acquiring a magnetic resonance (MR) image using the one or more imaging parameters.

Alternatively or additionally, selecting one or more imaging parameters can include adjusting at least one of a number of acquisition train per repetition time, resolution along a phase encoding direction, partial Fourier acquisition, or k-space under-sampling parameter (e.g., compressed sensing).

An example method for optimizing imaging parameters is also described herein. The method can include receiving at least one of magnetic resonance imaging (MRI) scanner settings for an imaging sequence, an acquisition train length, or a k-space strategy; determining one or more magnetic resonance (MR) parameters of a region of interest; using the one or more MR parameters, simulating respective relationships among an objective function and one or more imaging parameters; and selecting optimal imaging parameters associated with an optimal objective function.

Alternatively or additionally, the method for optimizing imaging parameters can further include acquiring a magnetic resonance (MR) image using the optimal imaging parameters.

Alternatively or additionally, an acquisition train includes at least one of a series of radiofrequency pulses acquisition (e.g., MPRAGE), refocusing radiofrequency pulse acquisition (e.g., fast echo spin), and bipolar gradient acquisition (e.g., echo planar imaging).

Alternatively or additionally, MRI scanner settings can include at least one of receiver bandwidth, parallel imaging techniques, partial Fourier, transmit bandwidth, navigation, trigger options, multi-nuclear options, or saturation band.

Alternatively or additionally, an objective function can include at least one of a contrast metric, a signal intensity metric, or an artifact metric. A contrast metric can include, but is not limited to, contrast, contrast-to-noise ratio (CNR) or CNR efficiency. A signal intensity metric can include, but is not limited to, signal intensity, signal-to-noise ratio (SNR) or SNR efficiency. An artifact metric can include, but is not limited to, noise, signal inhomogeneity, SNR inhomogeneity, contrast inhomogeneity, CNR inhomogeneity, signal loss, geometry distortion or image ghost, or motion artifact.

Alternatively or additionally, imaging parameters can include at least one of a repetition time (TR), echo time (TE), flip angle, refocusing flip angle, magnetization preparation pulses, fat saturation pulses, inversion times, bandwidth, echo train length, echo space time or readout RF number.

Alternatively or additionally, a region of interest can include at least a portion of a subject's body with or without disease. Optionally, the portion of the subject's body can be at least one of an extremity, brain, spine, neck, chest, breast, joint, prostate, pelvis, or abdomen. This disclosure contemplates that the region of interest can include a portion of an extremity, brain, spine, neck, chest, breast, joint, prostate, pelvis, or abdomen.

Alternatively or additionally, the imaging sequence can include at least one of two spatial dimensional, three spatial dimensional, or three spatial dimensional plus temporal image acquisition. Alternatively or additionally, the imaging sequence can include at least one of a gradient echo, echo planar or spin echo sequence with or without magnetization preparation, with or without under-sampling techniques, with or without parallel imaging techniques, or with or without Cartesian k-space trajectories.

Alternatively or additionally, the one or more MR parameters can change based on at the least one of an age, a pathophysiological change, a physiological change, an electrophysiological change, a disease in tissue, an implanted or injected material, or in-take of medicine. Alternatively or additionally, the one or more MR parameters can include at least one of $T_1$ relaxation, $T_2$ relaxation, $T_2$ star relaxation, proton density, diffusion, magnetic susceptibility, oxygen/deoxygenated-hemoglobin, or magnetization transfer.

Alternatively or additionally, the acquired image can be at least one of a magnitude image, a phase image, a real image, an imaginary image, or a complex image. Alternatively or additionally, the acquired image can be at least one of an image of a fetus, preterm newborn, full-term newborn, neonate, infant, child, adult, or aging subject with and without disease in a region of interest.

Optionally, the methods described herein can further include using the acquired image for diagnosis, prognosis, surrogate endpoint, or therapeutic response. Alternatively or additionally, the methods described herein can further include using the acquired image for computer-aided diagnosis. The computer-aided diagnosis can include a quantification of at least one of volumetric, image intensity, or surface of at least a portion of a region of interest, perfusion, blood volume, flow velocity, relaxation time, diffusion coefficient, proton density, or electro-magnetic properties.

Alternatively or additionally, the disease for the fetus or placenta can be one or more of tumor, suspected cancer, white matter injury, congenital brain abnormalities, vascular malformations, monochorionic twin pregnancy complications, neural tube defects, caudal regression syndrome, vertebral anomalies, facial clefts, congenital diaphragmatic hernia, congenital pulmonary airway malformation, congenital heart malformation, brain hemorrhage, ventriculomegaly, hydrocephalus, congenital stroke, congenital infections, traumatic brain injury, or suspected drug effects.

Alternatively or additionally, the disease for the preterm and full-term newborn or infant subject can be one or more of tumor, white matter injury, subcortical gray matter injury, cortical brain injury, hypoxic-ischemic encephalopathy, congenital/perinatal/neonatal stroke, ventriculomegaly, hydrocephalus, metabolic disorders, congenital brain abnormalities, encephalopathy of prematurity, delayed brain maturation, punctate white matter lesions, periventricular leukomalacia, diffuse excessive high signal intensity, intraventricular hemorrhage, other brain hemorrhages, multiple punctate lesions, venous thrombosis, infectious disorders, calcifications, congenital diaphragmatic hernia, congenital pulmonary airway malformations, congenital heart malformations, vascular malformations, congenital stroke, meningomyelocele, traumatic brain injury, suspected drug effects, or neonatal seizures.

Alternatively or additionally, the disease for the child subject can be one or more of tumor, stroke/ischemia, chronic vascular disease, vascular malformations, arterial or venous/dural venous sinus abnormalities, congenital brain abnormalities, congenital or acquired hydrocephalus, metabolic, disorders, trauma, hemorrhage, inflammatory and autoimmune disorders, infectious disorders, endocrine disorders, evaluation of cranial nerves, psychiatric disorders, assessment of iatrogenic sequelae, image guidance for treatment planning, surgery, or interventional, chronic headaches, migraines, peripheral nervous system disorders, congenital heart disease, pulmonary disorders, inflammatory bowel disease, joint disease/injury, or evaluation of poisoning.

Alternatively or additionally, the disease of adult or aging subjects can be one or more of tumor, multiple sclerosis, Alzheimer diseases, Psychopathy, Parkinson, atrophy, Huntington's disease, Bipolar disorder, or stroke.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

As shown in FIG. 3, CNR efficiency is greatest with an ATL of 90 and reaches its maximum at a $TI_{eff}$ of ~1600.

FIG. 7 is a flow diagram illustrating an example method for optimizing k-space strategy as described herein.

FIGS. 8(a) and 8(b) are graphs illustrating simulated signal intensity of the cerebrospinal fluid (CSF) (FIG. 8(b)) and gray matter-white matter (GM-WM) (FIG. 8(a)) contrast for different positions of the $i^{th}$ read-out RF pulse at different time intervals (TIs) of a neonatal brain image acquired with the MPRAGE sequence.

FIG. 9 is a flow diagram illustrating an example method for optimizing imaging parameters as described herein.

FIG. 19 shows images of a very preterm infant at term with hemorrhage and secondary focal porencephalic changes within the right frontal white matter (shown by arrows in FIG. 19). The images were acquired using the optimized MRI protocol described herein.

FIG. 20 shows images of a one week old full-term infant with moderate scattered subdural and subarachnoid bleeding likely related to childbirth (shown by arrows in FIG. 20). The images were acquired using the optimized MRI protocol described herein.

FIG. 21 shows images of an extremely preterm infant term with sequelae of bilateral intraventricular hemorrhages with resulting porencephalic changes and posthemorrhagic hydrocephalus (shown by arrows in FIG. 21). The images were acquired using the optimized MRI protocol described herein.

FIG. 23 shows images of a very preterm infant at term with bilateral frontal lobe diffuse white matter abnormality (aka diffuse excessive high signal intensity) (shown by arrows in FIG. 23). The images were acquired using the optimized MRI protocol described herein.

FIG. 26 shows images of an eight day old full-term infant with acute/subacute infarct in the left basal ganglia following prolonged childbirth and birth asphyxia. Findings are consistent with hypoxic ischemic encphalopathy (shown by arrows in FIG. 26). The images were acquired using the optimized MRI protocol described herein.

FIG. 27 is a block diagram illustrating an example computing device.

DETAILED DESCRIPTION

Figure 1:
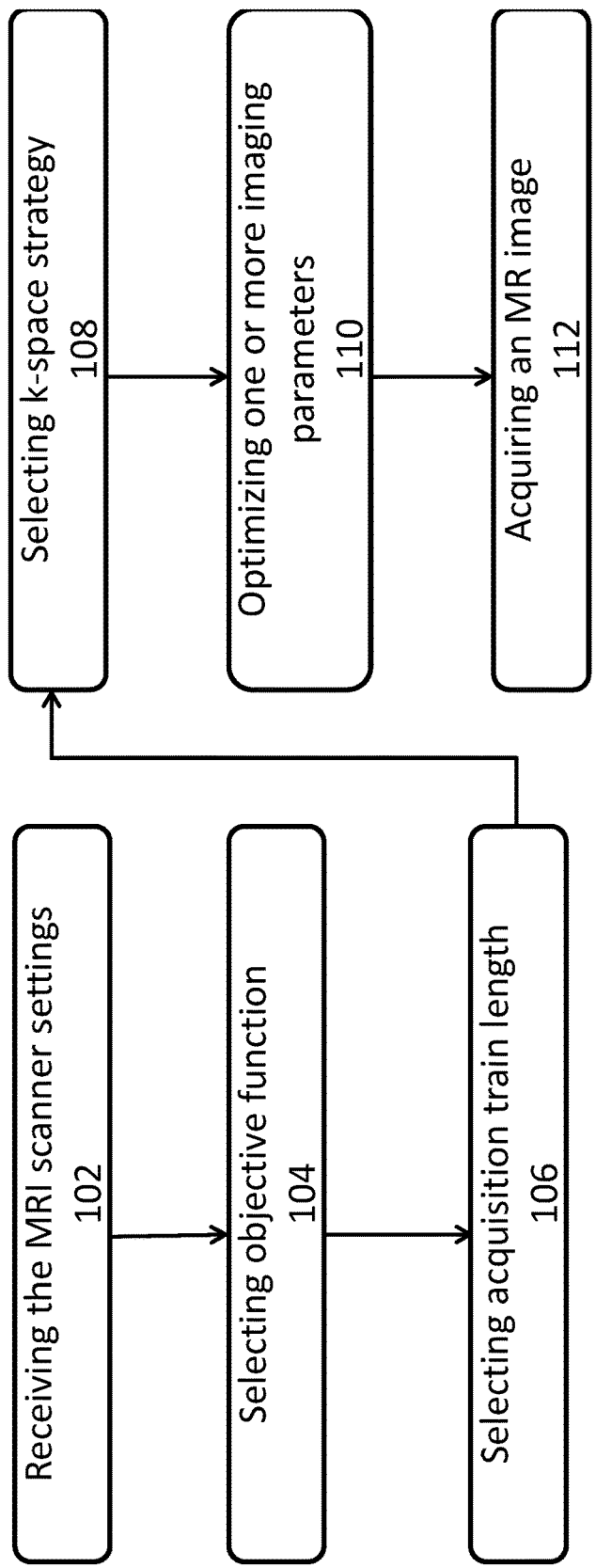
FIG. 1 is a flow diagram illustrating an example method for optimizing an MRI protocol as described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for optimizing MRI scanner settings (also referred to herein as "basic scanner settings"), MRI protocols, acquisition train length, k-space strategy, and/or imaging parameters with regard to MRI modalities, it will become evident to those skilled in the art that the implementations are not limited thereto, but are applicable to other image modalities such as, computed tomography, for example. Additionally, this disclosure contemplates that MRI modalities include MRI techniques with administration of contrast agents, for example, contrast enhanced MR angiography. This disclosure contemplates that the images obtained using the techniques described herein can be directly employed in at least one of diagnosing diseases, monitoring prognosis and therapeutic responses, conducting treatment plans, and improving quantification of MRI. For example, the techniques described herein can be used for the diagnoses of specific diseases such as the standardization of the MRI protocol in The Alzheimer's Disease Neuroimaging Initiative. Additionally, the techniques described herein are optionally applicable to a group of individuals in a similar pathophysiological situation.

As used herein, an acquisition train can include, but is not limited to, at least one of a series of radiofrequency pulses acquisition (e.g., MPRAGE), refocusing radiofrequency pulse acquisition (e.g., fast echo spin), and bipolar gradient acquisition (e.g., echo planar imaging).

Alternatively or additionally, Mill scanner settings can include, but are not limited to, at least one of receiver bandwidth, parallel imaging techniques, partial Fourier, transmit bandwidth, navigation, trigger options, multi-nuclear options, or saturation band.

Alternatively or additionally, an objective function can include, but is not limited to, at least one of a contrast metric, a signal intensity metric, or an artifact metric, including combinations thereof. A contrast metric can include, but is not limited to, contrast, contrast-to-noise ratio (CNR) or CNR efficiency. A signal intensity metric can include, but is not limited to, signal intensity, signal-to-noise ratio (SNR) or SNR efficiency. An artifact metric can include, but is not limited to, noise, signal inhomogeneity, SNR inhomogeneity, contrast inhomogeneity, CNR inhomogeneity, signal loss, geometry distortion or image ghost, or motion artifact.

Alternatively or additionally, imaging parameters can include, but are not limited to, at least one of a repetition time (TR), echo time (TE), flip angle, refocusing flip angle, magnetization preparation pulses, fat saturation pulses, inversion times, bandwidth, echo train length, echo space time or readout RF number.

Alternatively or additionally, a region of interest can include, but is not limited to, at least a portion of a subject's body with or without disease. Optionally, the portion of the subject's body can be at least one of an extremity, brain, spine, neck, chest, breast, joint, prostate, pelvis, or abdomen. This disclosure contemplates that the region of interest can include a portion of an extremity, brain, spine, neck, chest, breast, joint, prostate, pelvis, or abdomen.

Alternatively or additionally, the imaging sequence can include, but is not limited to, at least one of two spatial dimensional, three spatial dimensional, or three spatial dimensional plus temporal image acquisition. Alternatively or additionally, the imaging sequence can include, but is not limited to, at least one of a gradient echo, echo planar or spin echo sequence with or without magnetization preparation, with or without under-sampling techniques, with or without parallel imaging techniques, or with or without Cartesian k-space trajectories.

Alternatively or additionally, the one or more MR parameters can change based on at the least one of an age, a pathophysiological change, a physiological change, an electrophysiological change, a disease in tissue, an implanted or injected material, or in-take of medicine. Alternatively or additionally, the one or more MR parameters can include, but are not limited to, at least one of $T_1$ relaxation, $T_2$ relaxation, $T_2$ star relaxation, proton density, diffusion, magnetic susceptibility, oxygen/deoxygenated-hemoglobin, or magnetization transfer.

Alternatively or additionally, the acquired image can be at least one of a magnitude image, a phase image, a real image, an imaginary image, or a complex image. Alternatively or additionally, the acquired image can be at least one of an image of a fetus, preterm newborn, full-term newborn, neonate, infant, child, adult, or aging subject with and without disease in a region of interest.

Alternatively or additionally, the disease for the fetus or placenta can be one or more of tumor, suspected cancer, white matter injury, congenital brain abnormalities, vascular malformations, monochorionic twin pregnancy complications, neural tube defects, caudal regression syndrome, vertebral anomalies, facial clefts, congenital diaphragmatic hernia, congenital pulmonary airway malformation, congenital heart malformation, brain hemorrhage, ventriculomegaly, hydrocephalus, congenital stroke, congenital infections, traumatic brain injury, or suspected drug effects.

Alternatively or additionally, the disease for the preterm and full-term newborn or infant subject can be one or more of tumor, white matter injury, subcortical gray matter injury, cortical brain injury, hypoxic-ischemic encephalopathy, congenital/perinatal/neonatal stroke, ventriculomegaly, hydrocephalus, metabolic disorders, congenital brain abnormalities, encephalopathy of prematurity, delayed brain maturation, punctate white matter lesions, periventricular leukomalacia, diffuse excessive high signal intensity, intraventricular hemorrhage, other brain hemorrhages, multiple punctate lesions, venous thrombosis, infectious disorders, calcifications, congenital diaphragmatic hernia, congenital pulmonary airway malformations, congenital heart malformations, vascular malformations, congenital stroke, meningomyelocele, traumatic brain injury, suspected drug effects, or neonatal seizures.

Alternatively or additionally, the disease for the child subject can be one or more of tumor, stroke/ischemia, chronic vascular disease, vascular malformations, arterial or venous/dural venous sinus abnormalities, congenital brain abnormalities, congenital or acquired hydrocephalus, metabolic, disorders, trauma, hemorrhage, inflammatory and autoimmune disorders, infectious disorders, endocrine disorders, evaluation of cranial nerves, psychiatric disorders, assessment of iatrogenic sequelae, image guidance for treatment planning, surgery, or interventional, chronic headaches, migraines, peripheral nervous system disorders, congenital heart disease, pulmonary disorders, inflammatory bowel disease, joint disease/injury, or evaluation of poisoning.

Alternatively or additionally, the disease of adult or aging subjects can be one or more of tumor, multiple sclerosis, Alzheimer diseases, Psychopathy, Parkinson, atrophy, Huntington's disease, Bipolar disorder, or stroke Techniques are described herein where MRI scanner settings are considered to optimize a plurality of objective functions, particularly for acquisition train length. In addition, if k-space optimization is available, the optimized k-space strategy is determined based on one or more objective functions. For a given MRI scanner setting and k-space strategy, imaging parameters are optimized to achieve optimized objective functions. The initial optimized imaging parameters are determined using simulated objective functions and then optionally modified and confirmed using in vivo experiments. Final images in the image domain can be applied in clinical and research settings to improve diagnosis of diseases, determine prognosis of diseases, and monitor therapeutic response.

Techniques are described herein for optimizing MRI protocols (e.g., including MRI scanner settings, acquisition train length, image resolution, optimization of imaging parameters for specific objective functions, and k-space strategies). The techniques can enhance image quality and improve detection sensitivity of pathophysiological changes in fetuses, neonates, infants, children and/or adults. The optimized MRI protocols in combination with various existing techniques (such as motion reduction, contrast operations and tissue selections) are described herein.

Techniques are described herein for optimizing MRI protocols for acquiring high quality MRI images. For example, a method for initial optimization of MRI scanner settings for a given hardware and software system is described. Additionally, a method to simulate acquisition train length and objective functions (such as signal intensity, noise, and contrast) using an analytic and/or empirical and/or approximated solution of Bloch Equations with tissue MR parameters are described. The optimized acquisition train length is determined by the objective functions. A method for optimizing k-space strategies is performed to simulate k-space strategies and objective functions using the solution of Bloch Equations with tissue MR parameters. The optimized k-space strategy is determined by the objective function for a particular application. Techniques are described herein for optimizing imaging parameters for given MRI scanner settings, acquisition train length, and k-space strategies. For the optimized protocols, enabling accurate interpretation of the acquired images by radiologists or computer-aided diagnostics is considered in selecting the optimized objective functions.

Additionally, techniques are described herein for k-space optimization. K-space optimization is based on MRI scanner settings, which include hardware and software configuration, and k-space trajectory (e.g., rectangle, radial and random). K-space optimization includes simulating the relationship between each respective k-space acquisition and an objective function (e.g., an image quality metric such as a signal intensity metric, a contrast metric, or an artifact metric) according to Bloch Equations. K-space optimization is available for sequences in which each respective k-space acquisition has a different image quality (or other objective function) as that used for k-space optimization, such as MPRAGE, echo planar imaging and fast spin echo sequences. On the other hand, if each k-space acquisition has an identical image quality (or other objective function) as that used for k-space optimization, such as gradient echo, FLASH and spin echo sequences, k-space strategies cannot be optimized. In other words, a prerequisite of k-space optimization is that each respective k-space acquisition has a different objective function as that used for k-space optimization. Additionally, during k-space optimization, parameters can be limited to those permitted by the clinically-available MRI scanners.

Additionally, techniques are described herein for optimizing imaging parameters so that high quality MR images can be acquired using existing MRI facilities. This can be achieved through simulations and iterative experiments including the following steps: obtaining one or more MR parameters for a normal or pathological (e.g., diseased) tissue; simulating at least one objective function for the MRI sequence with the MR parameters of the tissue, where objective function includes signal intensity metric, contrast metric, noise, artifact metric, (or any other objective function including those described herein); optimizing one or more imaging parameters based on the optimized objective function; and acquiring MR images using the optimized imaging parameters.

Optionally, the MRI sequence can be any sequence for acquiring magnetic resonance (MR) images of a subject/or object with acceptable spatial-temporal resolution. For example, the MRI sequence can be any one of gradient echo sequence (e.g., including the MP-RAGE sequence), echo planar sequence, spin echo sequence, and rapid acquisition relation enhanced imaging sequence (e.g., turbo spin echo, fast spin echo). The MRI sequence can also be combined with one or more of parallel imaging technique, compress sensing technique, and/or contrast agent. It should be understood, however, that the above MRI sequences are provided only as examples and that this disclosure contemplates using other MRI sequences.

Optionally, the images acquired with the optimized MRI protocol can be any MR images. For example, the acquisitions can be two spatial dimensional, three spatial dimensional or three spatial plus temporal and thus four-dimensional images. The images can be also at least one of magnitude images, phase images, real images, imaginary images, complex images, including combinations thereof. It should be understood, however, that the above images are provided only as examples and that this disclosure contemplates acquiring other types of MR images.

Optionally, the one or more imaging parameters include, but are not limited to, a repetition time (TR), an echo time (TE), a flip angle, a refocusing flip angle, magnetization preparation pulses, fat saturation pulses, inversion times, a bandwidth, an echo train length, an echo space time or a readout RF number. It should be understood, however, that the above imaging parameters are provided only as examples and that this disclosure contemplates optimizing other imaging parameters. Alternatively or additionally, the one or more imaging parameters are within predetermined ranges imposed by hardware system or safety limitations. For example, the hardware system (e.g., one or more magnets and gradient strength thereof, RF coil, acquisition bandwidth, etc.) can limit the range of useable imaging parameters. Similarly, safety limitations such as specific absorption rate or nerve stimulation can also limit the range of useable imaging parameters. This disclosure contemplates that the optimized imaging parameters can be selected from within the predetermined ranges. Optionally, the one or more imaging parameters facilitate detection of at least one of a pathophysiological change, physiological change, electrophysiological change or disease in tissue.

Optionally, the objective function includes, but is not limited to, a signal intensity metric (signal intensity, signal-to-noise ratio (SNR), SNR efficiency); a contrast metric (contrast, contrast-to-noise ratio (CNR) or CNR efficiency); an artifact metric (signal inhomogeneity, SNR inhomogeneity, contrast inhomogeneity, CNR inhomogeneity, signal loss, geometry distortion or image ghost), and their combinations. It should be understood, however, that the above objective functions are provided only as examples and that this disclosure contemplates other objective functions.

Optimally, the MRI scanner settings includes receiver bandwidth, parallel imaging technique, partial Fourier, transmit bandwidth, navigation, trigger options, multinuclear options, and saturation bands. The optimization of MRI scanner settings is determined by hardware limitations, MRI safety, optimal objective functions, and difficulty of implementation. It should be understood, however, that the above MRI scanner settings are provided only as examples and that this disclosure contemplates other MRI scanner settings.

Optionally, the acquisition train includes at least one of a series of radiofrequency pulses acquisition (MPRAGE or MP-RAGE), refocusing radiofrequency pulse acquisition (fast spin echo), and bipolar gradient acquisition (echo planar imaging).

Optionally, the acquisition train length can be adjusted using at least one of a number of acquisition train per repetition time, resolution along phase encoding direction, partial Fourier acquisition, and other k-space under-sampling techniques.

Optionally, the MR parameters are static field strength and pathophysiology dependent. It is also dependent of the properties of normal or abnormal tissues. For example, the MR parameters include, but are not limited to, $T_1$ relaxation, $T_2$ relaxation, $T_2$ star relaxation, proton density, diffusion, magnetic susceptibility, oxygenated/deoxygenated-hemoglobin or magnetization transfer. This disclosure contemplates that the MR parameters can include other parameters related to objective functions. It should be understood that the MR parameters could be obtained from the literature and/or estimated from experimental results.

Optionally, the MRI images are acquired using an optimal k-space strategy or a predetermined k-space strategy for long train acquisition.

Most MR image information (e.g., contrast and general shape) is contained in the center of the k-space. The low-spatial-frequency components in the center of the k-space have the highest amplitudes, giving rise to the greatest changes in image contrast. High-spatial-frequency components in the periphery of the k-space have lower amplitudes. These high-spatial-frequency components have little effect on image contrast or general shape but sharpen the image as they encode edges. The higher the spatial frequency the k-space covers, the higher the spatial resolution of the image is. Therefore, the k-space zero line largely determines image contrast. With a rectilinear k-space trajectory, there are three k-space sampling orders: sequential order, centric order, and reverse centric order. K-space strategy cannot be optimized in conventional gradient echo, spin echo and steady state acquisition. It can only be optimized in echo train without steady-state acquisition. The optimal k-space strategy is: (1) determined by the effective TE and/or TI (inversion recovery time), or (2) determined by the objective functions. For example, the contrast of images acquired with a fast spin echo sequence with perfect refocusing pulses is determined by the choice of effective TE. For example, the optimal k-space strategy for MRPAGE acquisition of adult brain images is determined by CNR and/or CNR efficiency, as described in U.S. 2015/0071514, filed Sep. 10, 2013, entitled "METHODS AND DEVICES FOR OPTIMIZATION OF MAGNETIC RESONANCE IMAGING PROTOCOLS." According to the methods and systems described herein, k-space strategy optimization is extended to any echo train without steady-state acquisition. The optimal k-space strategy is determined by objective functions that include not only image quality metrics, but also noise and artifacts. The extended k-space strategy optimization can be applied to a broad range of situations, including sequences, regions of interest, different age groups and non-Cartesian acquisition. Additionally, the optimization of k-space strategies can account for trade-offs of different objective functions described herein.

Optionally, the k-space strategy includes a k-space trajectory and a sampling order. An example sampling order is an order consistent with the order which lower spatial-frequency k-space is corresponding to higher contrast metric, for example. The k-space trajectory can include at least one of rectilinear, radial, echo planar imaging, spiral, projection reconstruction, random k-space trajectory, under-sampled k-space trajectory, and partial k-space sampling trajectory. The sampling order can include at least one of a sequential, centric, interleave, reverse or random sampling order. Optionally, the optimal k-space strategy is the k-space trajectory and sampling order that achieves at least one optimal objective function, for example, as determined by computer simulation. Optionally, a trade-off among objective functions is considered for determining the optimal k-space strategy, particularly if k-space zero line filling leads to large image artifacts.

Alternatively or additionally, simulating the relationship between each respective k-space acquisition and at least one objective function optionally further includes using an analytical and/or empirical and/or approximated solution of Bloch Equations for the imaging sequence and tissue MR parameters.

Optionally, the optimization of imaging parameters is performed after the optimization of the MRI scanner settings and k-space strategy. Optimization of the imaging parameters is an important step for MRI protocol optimization. The optimization of imaging parameters can be achieved with the following steps: (1) simulating the relationship between the imaging parameters and objective functions for a given MRI scanner setting and k-space strategy using an analytical and/or empirical and/or approximated solution of Bloch Equations; (2) simulating the relationship for regions of interests with tissue MRI parameters; and (3) determining the optimal imaging parameters using the optimal objective function based on potential applications of the acquired images. Thereafter, images can be acquired using the optimal imaging parameters.

Optionally, MR parameters can be changed by various factors, such as the subject's age, a pathophysiological, physiological, electrophysiological change or disease in tissue, implanted materials, in-take of medicine and injected materials. These factors can be considered in optimizing the imaging parameters.

Alternatively or additionally, the method can further include refining or adjusting the optimized imaging parameters based on the acquired MR images.

Optionally, the described herein can be applied in at least a portion (e.g., whole and/or part) of a subject's (such as a human, for example) body, including brain, spine, neck, chest, breast, joint, extremities, prostate, pelvis, and abdomen, with or without disease.

Optionally, the images acquired with the optimal imaging parameters can be directly used by radiologists and physicians for diagnosing disease, determining disease prognosis, and/or monitoring therapeutic response. The objective functions can be adjusted for different objectives of applications so that the best image quality can be achieved for the objectives.

Alternatively or additionally, the images acquired with the optimal imaging parameters can be used in computer-aided diagnosis to estimate volumetric, surface, perfusion, blood volume, flow velocity, relaxation time, diffusion coefficient, proton density, and electro-magnetic properties to improve diagnosis, determine prognosis, and monitor therapeutic responses.

Described herein are methods and devices where MRI scanner settings are considered to optimize a plurality of objective functions. The MRI scanner settings can include at least one of receiver bandwidth, parallel imaging techniques, partial Fourier, transmit bandwidth, navigation, trigger options, multi-nuclear options, or saturation band. For example, narrow receive bandwidth can be selected to minimize noise in the present disclosure.

In fast spin echo acquisition, the high spatial frequency components are attenuated with long echo train length, and then result in image blurring. In the present disclosure, however, shortening the acquisition train length along the slice direction can be used to improve SNR and CNR efficiencies. Experimental results have also showed that, for images acquired with MP-RAGE, reduced acquisition train length can attenuate the high spatial frequency components as increased acquisition train length does in fast spin echo. The major reason for this discrepancy is that with long acquisition train length, $T_1$ recovery dominates in MP-RAGE scans, whereas $T_2$ decay dominates in fast spin echo scans. Additionally, slice partial Fourier acquisition along the slice direction can reduce the magnitude of high spatial frequency components. In this case, other methods can be applied to reduce acquisition train length. For example, parallel acquisition techniques or increased slice thickness or k-space under-sampling can be applied to shorten acquisition train length for identical brain coverage In addition, if k-space optimization is available, the optimal k-space strategy is determined based on optimal objective functions. For a given MRI scanner setting and k-space strategy, imaging parameters are optimized to achieve optimal objective functions. The initial optimal imaging parameters are determined using simulated objective functions and then optionally modified and confirmed using in vivo experiments. Final images in image domain can be applied in clinical and research settings for improving diagnosis of various diseases, determining prognosis, and monitoring therapeutic response.

Early methods for optimizing imaging parameters focused on maximizing SNR, which resulted in SNRs far in excess of what is required to detect pathologies being investigated in current clinical MRI systems. SNR is the most important objective function in optimizing MR protocols for acquiring MR images with high spatial resolution, high temporal resolution, low field strength, low nuclei density and fast imaging techniques. But when SNR for regions of interest reach a reasonable value, the contrast between normal and disease tissues, not the SNR, is a better metric for diagnostic sensitivity and specificity of the disease. According to the methods and systems for optimizing MRI protocols described herein, it is possible to optimize the objective functions which include signal metric (e.g. signal, signal-to-noise ratio (SNR), or SNR efficiency), contrast metric (e.g. contrast, contrast-to-noise ratio (CNR), or CNR efficiency), and image artifact metric (e.g. signal loss, geometry distortion or image ghost, or motion artifacts). In most cases, it is very difficult to find initial optimal imaging parameters for optimizing all objective functions simultaneously, and thus the initial optimal imaging parameters are chosen in consideration of the trade-offs between multiple objective functions. Typically, imaging parameters are iteratively optimized through experimentation with multiple scans of a subject. Because the process is very time-consuming and cost-intensive, particularly with long acquisition times, the experimental approach is usually not practical in clinical settings. In the techniques described herein, a plurality of objective functions, including but not limited to signal intensities, for interested tissues are numerically estimated, for example, using Bloch's equations with tissue MR parameters that are either directly measured or obtained from the literature. The initial optimized image parameters can be determined based on maximizing tissue contrasts and minimizing artifacts as well as noise. The optimized imaging parameters can then be refined using measurements from in vivo experiments based on the initial optimized image parameters.

MR images are reconstructed by an inverse 2D or 3D fast Fourier transform (FFT) from raw data, which are collected in the spatial frequency domain (the "k-space"). Optimal k-space strategy, including sampling trajectory and order, is a factor in enhancing image quality when regions of k-space have different contrasts for echo train acquisition. It is known that k-space zero line sampling is one of the major factors that determine image contrast. If all k-space lines have the same contrast, for example in FLASH sequence acquisition, k-space zero line filled with any acquired k-space line will not change image contrast. If each k-space line corresponds to a different contrast, k-space zero line filled with different acquired k-space lines will lead to different image contrasts. In most cases, the operator may not be able to ascertain the suitability of a sampling trajectory and order without an unduly large number of trials. According to techniques described herein, k-space strategy optimization is performed using numerical simulations for at least one objective function or a combination of multiple objective functions, with great savings on time and costs. For example, CNR and CNR efficiency can be used as an objective function to optimize k-space strategy of magnetization preparation gradient echo (MPRAGE) for healthy adult brain at 3.0 T, as described in U.S. 2015/0071514, filed Sep. 10, 2013, entitled "METHODS AND DEVICES FOR OPTIMIZATION OF MAGNETIC RESONANCE IMAGING PROTOCOLS." After k-space strategy optimization, both CNR and SNR of the images acquired with the optimal imaging parameters have been greatly improved. When the k-space strategy of MPRAGE is optimized at low field strengths (such as 0.5 or 1.0 T scanners) signal intensity of some interested tissues may become comparable to noise. In that case, SNR will be used as an objective function.

MRI protocol optimization is important not only for image quality improvement and artifact reduction, but also for reducing the variability of images acquired across different sites and different time points in longitudinal studies. As for a given basic scanner setting and k-space strategy, the relationships among objective functions and imaging parameters can be simulated to determine the optimal imaging parameters based on the optimal objective function using analytical forms and approximated solution of Bloch Equations, and empirical formula of the imaging sequence with or without k-space optimization for regions of interest with MR parameters. The optimal imaging parameters can be determined by trade-offs among the objective functions (e.g., image quality, noise, and image artifacts), difficulty of implementation for technicians and MRI physicists, and image interpretation (e.g., radiologist interpretation and computer-aided diagnosis). The objective functions for imaging parameter optimization can include at least one of signal metric, contrast metric and artifact metric, as well as combinations thereof.

The MRI optimization techniques described herein can be applied to at least a portion of (e.g., a whole or part of) the human body with or without various diseases, including extremities, brain, spine, neck, chest, breast, joint, prostate, pelvis, and abdomen. The MR parameters used for the MRI protocol optimization can include $T_1$ relaxation, $T_2$ relaxation, $T_2$ star relaxation, proton density, diffusion, magnetic susceptibility, oxygenated/deoxgenated-hemoglobin or magnetization transfer. Moreover, MR parameters can vary with a person's age, a pathophysiological, physiological, electrophysiological change or disease in tissue, implanted materials, in-take of medicine and injected materials.

Images acquired with the optimized protocols can be directly used for radiologists' and physicians' diagnoses or for computer-aided diagnoses.

Example MR sequences (e.g., MPRAGE and FLASH sequences) are described below. It should be understood, however, that the MRI protocol optimization techniques described herein can be used with any sequence for acquiring MR images of a subject with acceptable spatial-temporal resolution. For example, the MRI sequence can be any one of gradient echo sequence (e.g., including the MP-RAGE sequence), echo planar sequence, spin echo sequence, and rapid acquisition relation enhanced imaging sequence (e.g., turbo spin echo, fast spin echo). The MRI sequence can also be combined with one or more of parallel imaging technique, compress sensing technique, and/or contrast agent. Thus, MP-RAGE and FLASH sequences are only described for example purposes.

MP-RAGE (or MPRAGE) Sequence

The MP-RAGE sequence is composed of 3D-inversion recovery a and N equally-spaced readout RF pulses of flip angle θ and echo spacing τ. Repetition time TR is defined as the time interval between two successive inversion recovery pulses as shown by Eq. 1 below:

$$TR = TI + N \cdot \tau + TD, \quad (1)$$

where τ is echo spacing time, N is the total number of readout RF pulses, TI is the time interval between the inversion recovery pulse and the first RF readout pulse, and TD is delay time. In order to simplify the formula for signal intensity, we define $\gamma = \exp(-TI/T_1)$, $\delta = \exp(-\tau/T_1)$ $\rho = \exp(-TR/T_1)$, $\varphi = \exp(-TD/T_1)$, and $\mu = \delta \cdot \cos(\theta)$. For successive excitations in the MP-RAGE sequence, signal intensity from the $i^{th}$ read-out pulse is given by Eq. 2 below:

$$s_i \propto M_i^- \cdot \sin(\theta) = \quad (2)$$

$$M_0 \cdot \sin(\theta) \cdot \left\{ \frac{(1-\delta)[1-\mu^{i-1}]}{1-\mu} + (\mu)^{i-1} \cdot (1-\gamma) - \gamma \cdot \mu^{i-1} \cdot \frac{M_{eq}}{M_0} \right\},$$

where the steady state magnetization $M_{eq}$ after several TRs is given by Eq. 3 below:

$$M_{eq} = \frac{1 - \varphi + \frac{\varphi \cdot \cos(\theta) \cdot (1-\delta)[1-\mu^{N-1}]}{1-\mu} + \varphi \cdot \cos(\theta) \cdot \mu^{N-1} + \rho \cdot \cos(\alpha) \cdot \cos^N(\theta)}{1 - \rho \cdot \cos(\alpha) \cdot \cos^N(\theta)} \cdot M_0, \quad (3)$$

The white matter (WM) and gray matter (GM) contrast from the $i^{th}$ read-out RF pulse is given by Eq. 4 below:

$$\text{Con}_{i,WM-GM} \propto s_{i,WM} - s_{i,GM}, \quad (4)$$

where $s_{i,WM}$ and $s_{i,GM}$ are the signal intensities of WM and GM, which can be calculated using Eq. 2 with the longitudinal relaxation times and protein densities of WM and GM, respectively. In Eq. 4, GM-WM contrast is a function of N, TI, τ, θ and the temporal position of the read-out RF pulse. Generally, the smaller the acquisition bandwidth is, the higher SNR and CNR are.

Although it is a property in the image domain that is determined by all Fourier components in the entire k-space, contrast between WM and GM is mostly determined by k-space center which are associated with the low spatial frequency components in k-space. According to Eqs. 2-4, GM and WM contrast from the $i^{th}$ read-out RF pulse is a function of the temporal position of the RF pulse and the total number of read-out RF pulses N. The major objective of k-space optimization is to optimize the k-space trajectory such that k-space center has the maximal $\text{Con}_{i,WM-GM}$. As described above, because the example scanner above has a few fixed k-space sampling settings, it was not possible to reach the theoretically optimal k-space sampling for MP-RAGE in experiments. Instead, the k-space sampling was optimized for the available settings on the example scanner.

Fast Low Angle Shot (FLASH) Sequence

The FLASH sequence is composed of a series of N equally-spaced readout RF pulses of flip angle θ at the repetition time TR. N is the total number of readout RF pulses, TI is inversion recovery time, and TD is delay time. In order to simplify the formula of signal intensity, we define $\alpha = \exp(-TR/T_1)$, and $\beta = \alpha \cdot \cos(\theta)$. For successive excitations in the FLASH sequence, the signal intensity after the $i^{th}$ excitation pulse is given using Eq. 5 below:

$$s_i \propto M_i \cdot \sin(\theta) = M_0 \cdot \sin(\theta) \cdot \frac{(1-\alpha)[1-\beta^{i-1}]}{1-\beta} \cdot S(x). \quad (5)$$

where $M_0$ is the equilibrium magnetization at the location x. It is very difficult to simulate the noise exactly because noise in MRI includes not only white noise but also physiological noise. Additionally, white noise is relatively stable in MR experiments. Thus, it is assumed that noise is stable at the different imaging parameters in the simulation. The WM-GM CNR efficiency (CNRef $f_{WM-GM}$) at a total scan time TA is given by Eq. 6 below.

$$CNReff_{WM-GM}(x) \propto \left[ M_{WM} \cdot \frac{1-\alpha_{WM}}{1-\beta_{WM}} - M_{GM} \cdot \frac{1-\alpha_{GM}}{1-\beta_{GM}} \right]. \quad (6)$$

$$\sin(\theta(x)) \cdot S(x) \cdot \frac{1}{\sqrt{TA}} \propto \left[ M_{WM} \cdot \frac{1-\alpha_{WM}}{1-\beta_{WM}} - M_{GM} \cdot \frac{1-\alpha_{GM}}{1-\beta_{GM}} \right].$$

$$\sin(\theta(x)) \cdot S(x) \cdot \frac{1}{\sqrt{TR}},$$

where $M_{WM}$ and $M_{WM}$ are the equilibrium magnetization of WM and GM, respectively. $\alpha_{WM} = \exp(-TR/T_{1,WM})$, $\alpha_{GM} = \exp(-TR/T_{1,GM})$, $\beta_{WM} = \alpha_{WM} \cdot \cos(\theta(x))$ and $\beta_{GM}=\alpha_{GM}\cdot\cos(\theta(x))$. $T_{1,WM}$ and $T_{1,WM}$ are the longitudinal relaxation times of WM and GM. The major objective of the optimization procedure is to maximize the contrast between WM and GM and reduce signal inhomogeneity using optimal imaging parameters (TR, θ) at a relatively short scan time. Since receive sensitivity S(x) is relative independent of imaging parameters (excluding receiver gain), it is assumed that sensitivity S(x)=1 in computer simulation of Eq. 6) was used as the objective function to determine the optimal imaging parameters in computer simulations.

Simulation of Optimized Imaging Parameters for Healthy Neonatal Brain

The MRI scanner settings (or "basic scanner settings") can be optimized according to the characteristics of the MRI scanner, for example, SIEMENS 3T SKYRA scanner of SIEMENS AG of MUNICH, GERMANY that was equipped with a 32-channel head coil. It should be understood that the SIEMENS 3T SKYRA scanner is provided only as an example and that other scanners can be used with the techniques described herein. Additionally, for the optimal basic scanner setting, 3D MPRAGE and conventional 3D gradient echo are optimized. The methods and systems for optimization of MRI protocols described herein are distinguishable from the method for MPRAGE optimization that is described in U.S.2015/0071514, filed Sep. 10, 2013, entitled "METHODS AND DEVICES FOR OPTIMIZATION OF MAGNETIC RESONANCE IMAGING PROTOCOLS" for at least a number of reasons. For example, the techniques described herein consider the effect of acquisition train length on image quality. Additionally, the optimization is performed after the optimization of basic scanner setting. Additionally, MR parameters are different. $T_1$, $T_2$, and proton density of the WM, GM and CSF of the neonatal brain at 3.0 T are 2840/2170/3700 ms, 266/138/2000 ms, and 0.94/0.90/1.0, respectively. Additionally, the objective functions are different. The objective functions include, but are not limited to, a signal metric, a contrast metric, and artifact metric, including combinations thereof. Additionally, the optimal imaging parameters are chosen in consideration of the trade-offs between multiple objective functions. Additionally, the k-space strategy can be chosen in consideration of the trade-offs between multiple objective functions. Additionally, MRI sequence optimization is extended to many MRI sequences, including but not limited to MPRAGE and FLASH. Additionally, according to the methods and systems described herein MRI sequences can be combined with various existing techniques, such as motion reduction techniques and tissue selection techniques. Additionally, MRI sequence optimization (e.g., MPRAGE optimization) is performed after k-space optimization, while current sequence optimization is performed after scanner setting optimization and/or selecting k-space strategies. That is, the imaging parameter optimization can be performed without k-space optimization. It should be understood that the differences above are provided only as examples and that other differences exist. In performing the simulations to optimize both k-space strategy and imaging parameters, relaxation effects during RF excitation were neglected and perfect spoiling of transverse magnetization was assumed after each inversion pulse and before each excitation pulse. Signal intensity, contrast and other objective functions of brain tissues were respectively simulated with Bloch Equations using programs written in MATLAB (MATH WORKS, INC., NATICK, Mass.). Here the MR parameters of diseased tissues are unknown. The optimal imaging parameters for diagnosing the diseases are not perfect. To further optimize the protocol for the diseases, at least SNR of the diseased tissue and tissues around it, and/or CNR between diseased tissue and the tissues around it are considered. Therefore, the MRI protocol for neonatal diseases can be further improved.

Simulation of Optimized Imaging Parameters for Adult Brains with Multiple Sclerosis (MS)

As for brain images of patients with MS, radiologists and physician are interested in detecting MS plaques. The detection of plaques is mainly determined by the contrast between WM and MS lesion. Effects of the major imaging parameters (e.g., number of readout RF pulses, flip angle, τ, TI, and TD) were simulated using Bloch's equations based on the values of $T_1$, $T_2$, and proton density of the WM and MS lesion of the adult brain, which at 3.0 T are 850-923/99/70 ms, and 1100-1400/104-107/77 ms, respectively (Kober, T., C. Granziera, et al. (2012). Invest Radiol 47(6): 346-352. Jurcoane, A., M. Wagner, et al. (2013). J Magn Reson Imaging 38(6): 1454-1461). Relaxation effects during RF excitation were neglected and perfect spoiling of transverse magnetization was assumed after each inversion pulse and before each excitation pulse. Signal intensity, contrast and other objective functions of the brain tissues were respectively simulated with Bloch Equations using programs written in MATLAB (MATH WORKS, INC., NATICK, Mass.). The optimal imaging parameters were determined based on the optimal objective function.

All infants were scanned within two weeks of birth on a SIEMENS 3T SKYRA scanner of SIEMENS AG of MUNICH, GERMANY that was equipped with a 32-channel head coil. It should be understood that the SIEMENS 3T SKYRA scanner is only provided as an example MRI scanner and that other MRI scanners can be used. All subjects were scanned during natural sleep after being fed, swaddled, and restrained using a Med-Vac vacuum fixation device (CFI Medical, Fenton, Mich.). MRI noise was minimized using Insta-Puffy Silicone Earplugs (E.A.R. Inc, Boulder, Colo.). Based on the computer simulations described above, optimized MP-RAGE imaging parameters were set to be: repetition time (TR)=2130 ms, effective inversion recovery time ($TI_{eff}$)=1610 ms, and flip angle (FA)=13°. Total scan time was 3 min, 32 s.

All MS patients were scanned on a SIEMENS 3T scanner that was equipped with a 32-channel head coil. It should be understood that the SIEMENS 3T SKYRA scanner is only provided as an example MRI scanner and that other MRI scanners can be used. The optimal basic scanner setting for MS patients are: receive bandwidth 140 Hz/pixel, matric 290×320×176, resolution 0.8 $mm^3$, FOV 232×256, and an acceleration factor of parallel acquisition of 2. Based on the computer simulations described above, the optimized MP-RAGE imaging parameters were set to be: repetition time (TR)=2420 ms, effective inversion recovery time (TIeff) =1400 ms, and flip angle (FA)=8°. Total scan time was 6 min 35 seconds. The images acquired using the optimized parameters were compared with the Siemens default imaging parameters: bandwidth 237 Hz/pixel, TR=2500 ms, TIeff=900 ms, FA=9°. Total scan time was 6 min 32 seconds.

Example Optimization Techniques

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

An example method for optimizing an MRI protocol can include optimizing one or more MRI scanner settings, selecting an optimal objective function from a plurality of objective functions based on the MRI scanner settings, and setting a k-space strategy. The method can also include optimizing one or more imaging parameters based on the optimal MRI scanner settings and the selected k-space strategy, and acquiring an image using the optimal imaging parameters.

Optionally, the method can include optimizing k-space strategies. K-space strategy optimization is not available for spoiled or full relaxation gradient echo, spin echo, or steady-state sequences with or without magnetization preparation or scanner limitation. K-space strategy optimization is available for echo train acquisition with and without magnetization preparation. The echo train acquisition can be echo planar imaging, fast spin echo imaging, or gradient echo imaging, for example.

Additionally, when k-space optimization is available, optimizing k-space strategies can include simulating respective relationships among at least one of the objective functions and the one or more imaging parameters, setting the k-space strategy to optimize the objective function, and acquiring the image using the optimal k-space strategy.

Alternatively or additionally, optimizing the imaging parameters can include computing respective relationships among at least one of the objective functions and the one or more imaging parameters to determine the optimal imaging parameters based on the optimal objective function. For example, the respective relationships can be computed based on: (i) analytical forms of Bloch's Equations or (ii) empirical formula of an imaging sequence with or without k-space optimization of a region of interest with one or more MR parameters or (iii) approximation solution of Bloch's Equations. For example, analytical solutions to Bloch Equations for fast spin echo are described in Lukzen N N, Saveloy A A, Analytical derivation of multiple spin echo amplitudes with arbitrary refocusing angle, J Magn Reson 2007, 185 (1):71-6. Numerical solutions to Bloch Equations are described in Murase K., Tanki N., Numerical solutions to the time-dependent Bloch equations revisited, Magn Reson Imaging 2011; 29(1):126-31. High tip angle approximation solutions to Bloch Equations are described in Boulant N1, Hoult DI, High tip angle approximation based on a modified Bloch-Riccati equation, Magn Reson Med 2012; 67(2):339-43. In other words, the simulation can be performed using Bloch Equations. Additionally, a solution of the Bloch's Equations can be at least one of an analytic solution, a numerical solution, or an approximation solution.

Described herein are techniques for optimizing a magnetic resonance imaging (MRI) protocol. An example method can include receiving one or more MRI scanner settings for an imaging sequence; selecting at least one objective function from a plurality of objective functions; selecting an acquisition train length; selecting a k-space strategy; selecting one or more imaging parameters; and acquiring a magnetic resonance (MR) image using at least one of an optimized k-space strategy, an optimized acquisition train length, or optimized imaging parameters. According to this example method, at least one of the k-space strategy, the acquisition train length, or the one or more imaging parameters can be optimized according to the techniques described herein.

Referring now to FIG. 1, a flow diagram illustrating example operations for optimizing an MRI protocol is shown. At 102, one or more MRI scanner settings for an imaging sequence are received. Optionally, the MRI scanner settings can be optimized for a given hardware and/or software system. At 104, at least one objective function from a plurality of objective functions can be selected. As described herein, the objective function can include, but is not limited to, a signal intensity metric, a contrast metric, or an artifact metric, including combinations thereof. At 106, an acquisition train length can be selected. In some implementations, the acquisition train length is a default acquisition train length of an MRI scanner or selected from acquisition train lengths of an MRI scanner. In other words, the acquisition train length is not optimized. In other implementations, the acquisition train length is optimized (e.g., as described herein with reference to FIG. 2). At 108, a k-space strategy can be selected based on the acquisition train length. In some implementations, k-space strategy is selected from available k-space strategies. In other words, k-space strategy is not optimized. In other implementations, k-space strategy is optimized (e.g., as described herein with reference to FIG. 7). At 110, one or more imaging parameters can be optimized. At 112, a magnetic resonance (MR) image can be acquired using at least one of the k-space strategy, the acquisition train length, or the one or more imaging parameters. The MR image can be acquired using optimized k-space strategy (e.g., as described with reference to FIG. 7), optimized acquisition train length (e.g., as described with reference to FIG. 2), and/or optimized imaging parameters (e.g., as described with reference to FIG. 9). This disclosure contemplates that the MR image can be acquired using one or more of k-space strategy, acquisition train length, and/or imaging parameters optimized as described herein.

Figure 2:
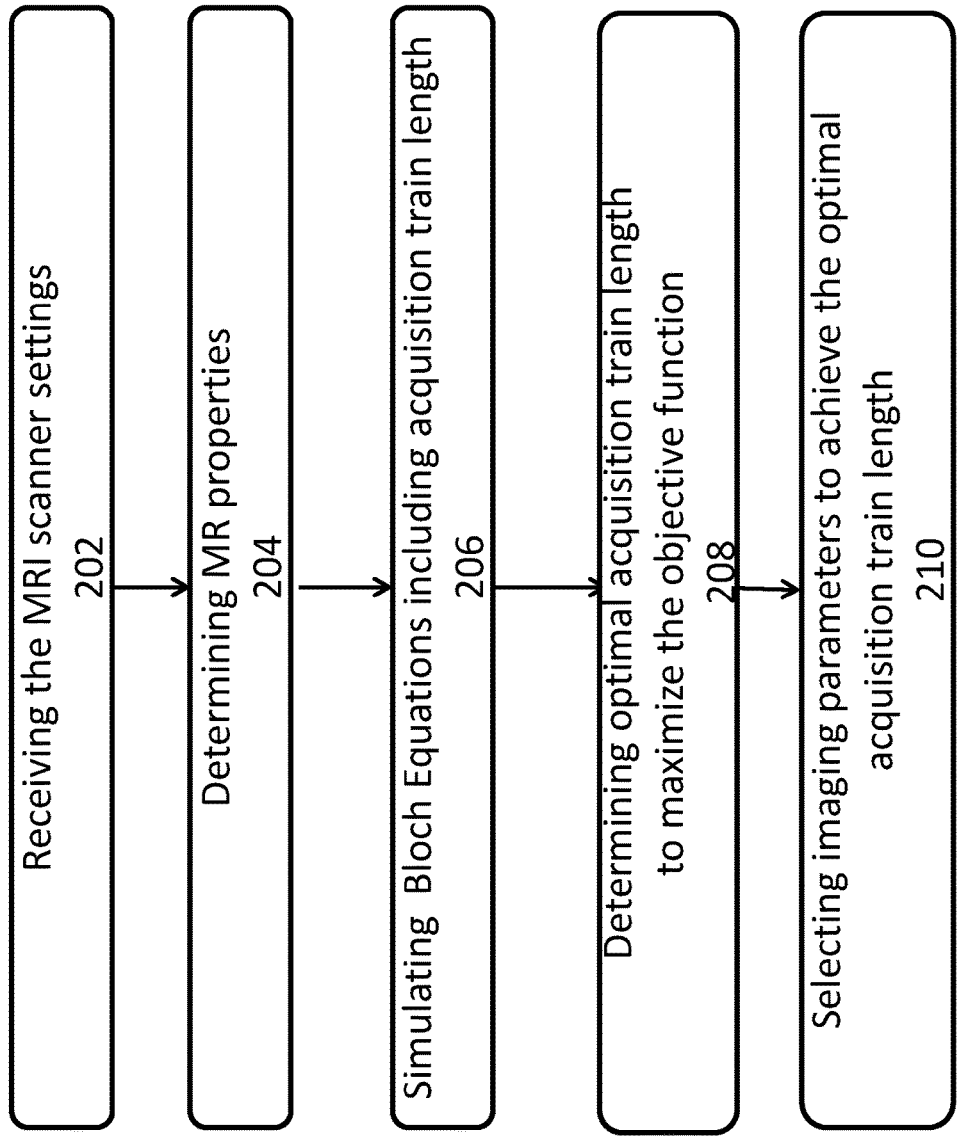
FIG. 2 is a flow diagram illustrating an example method for optimizing acquisition train length as described herein.

Referring now to FIG. 2, a flow diagram illustrating example operations for optimizing acquisition train length is shown. At 202, one or more magnetic resonance imaging (MRI) scanner settings for an imaging sequence can be received. At 204, one or more magnetic resonance (MR) parameters of a region of interest can be determined. At 206, using the one or more MR parameters, respective relationships among an acquisition train length and an objective function for the region of interest can be simulated. As described herein, the simulation can be performed using Bloch Equations. Additionally, a solution of the Bloch Equations can be at least one of an analytic solution, a numerical solution, or an approximation solution. At 208, the acquisition train length can be optimized to maximize the objective function for the region of interest. Then, at 210, one or more imaging parameters can be selected to achieve the optimal acquisition train length. Optionally, selecting one or more imaging parameters can include adjusting at least one of a number of acquisition train per repetition time, resolution along a phase encoding direction, partial Fourier acquisition, or k-space under-sampling parameter (e.g., compressed sensing). Alternatively or additionally, the method for optimizing acquisition train length can further include acquiring a magnetic resonance (MR) image using the one or more imaging parameters.

K-space strategy optimization is not available for sequences where each respective k-space acquisition has the same objective function (e.g., image quality) that is used for k-space optimization. Examples of such sequences include spoiled or full relaxation gradient echo, or spin echo sequences. Additionally, k-space strategy optimization is available for acquisition train length with and/or without magnetization preparation. Examples of such sequences include MPRAGE, echo planar imaging and fast spin echo sequences. Referring now to FIG. 7, a flow diagram illustrating example operations for optimizing k-space strategy is shown. At 702, one or more MRI scanner settings and an acquisition train length can be received. At 704, one or more magnetic resonance (MR) parameters of a region of interest can be determined. At 706, using the one or more MR parameters, respective relationships among the at least one objective function with the acquisition train length can be simulated. As described herein, the simulation can be performed using Bloch Equations. Additionally, a solution of the Bloch Equations can be at least one of an analytic solution, a numerical solution, or an approximation solution. At 708, the k-space strategy can be selected to optimize the at least one objective function. Then, at 710, the imaging parameters can be selected to achieve the optimal k-space strategy. Optionally, optimizing the k-space strategy can include optimizing the k-space filling order.

Referring now to FIG. 9, a flow diagram illustrating example operations for optimizing imaging parameters is shown. At 902, at least one of magnetic resonance imaging (MRI) scanner settings for an imaging sequence, an acquisition train length, or a k-space strategy can be received. At 904, one or more magnetic resonance (MR) parameters of a region of interest can be determined. At 906, using the one or more MR parameters, respective relationships among an objective function and one or more imaging parameters can be simulated. As described herein, the simulation can be performed using Bloch Equations. Additionally, a solution of the Bloch Equations can be at least one of an analytic solution, a numerical solution, or an approximation solution. Then, at 908, optimal imaging parameters associated with an optimal objective function can be selected. Optionally, the method for optimizing imaging parameters can further include acquiring a magnetic resonance (MR) image using the optimal imaging parameters.

This disclosure contemplates that the acquired image can be used for diagnosis, prognosis, surrogate endpoint, or therapeutic response. Alternatively or additionally, the acquired image can be used for computer-aided diagnosis. The computer-aided diagnosis can include a quantification of at least one of volumetric, image intensity, or surface of at least a portion of a region of interest, perfusion, blood volume, flow velocity, relaxation time, diffusion coefficient, proton density, or electro-magnetic properties.

Examples

Figure 3:
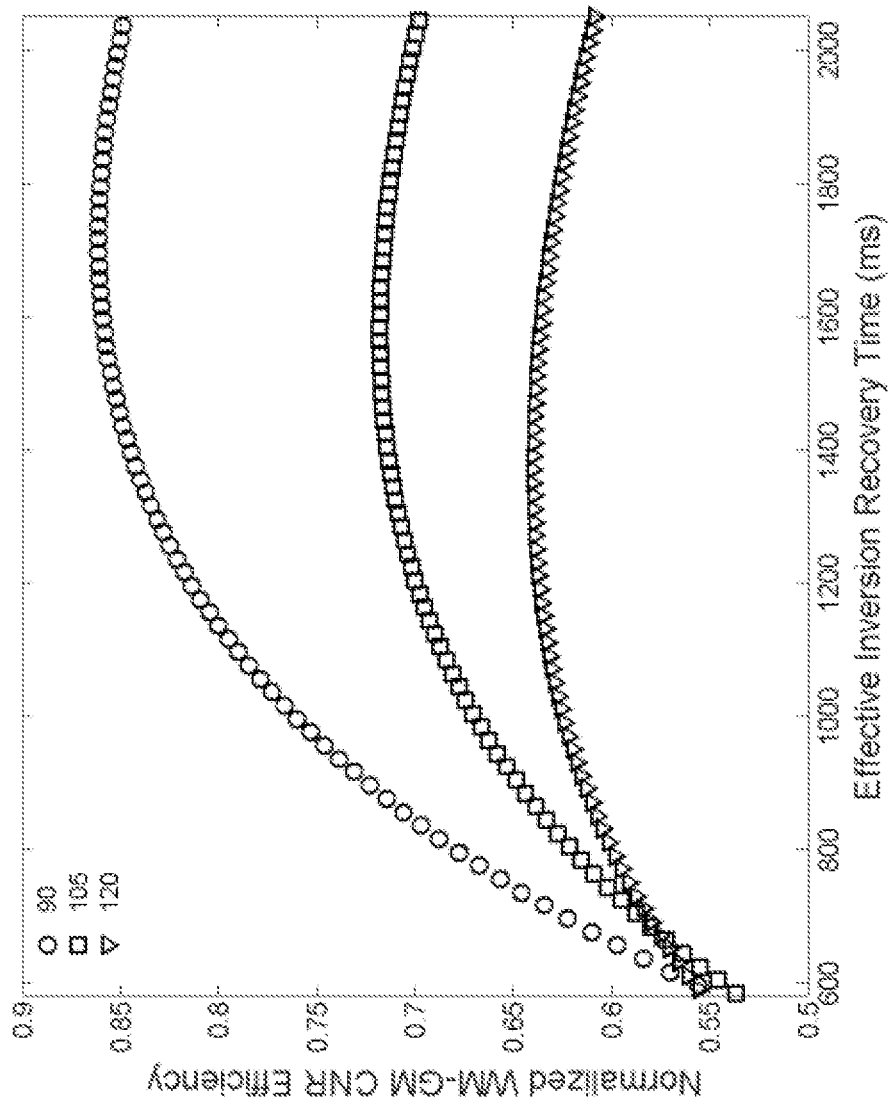
FIG. 3 is a graph illustrating simulated gray matter—white matter contrast to noise (CNR) efficiency as a function of effective inversion recovery time ($TI_{eff}$) with acquisition train lengths (ATL) of 120, 105 and 90.

The effects of acquisition train length (ATL) on image quality were investigated with consideration of balancing the tradeoff between ATL and spatial resolution. The desired spatial resolution was set to be 1 mm, at which, 120 slices are generally required to cover the whole neonatal brain. Then, slice partial Fourier was used to reduce ATL. In the settings of the 3T Siemens Skyra scanner, slice partial Fourier factors of 1, 7/8 and 6/8 correspond to ATL values of 120, 105 and 90, respectively. The theoretical effective inversion recovery time $TI_{eff}$ was computed for these ATLs with an echo spacing time of 8.5 ms (FIG. 3). The relative WM-GM contrast efficiency increased by approximately 40% when the ATL decreased from 120 to 90 (i.e. shortening ATL increased contrast efficiency). To summarize, simulation results suggest that the optimal ATL should be 90 with a corresponding optimal $TI_{eff}$ of 1610 ms at a spatial resolution of 1 mm.

As described herein, adjusting acquisition train length includes adjusting at least one of number of acquisition train per repetition time, resolution along phase encoding direction, partial Fourier acquisition, and other k-space undersampling.

Figure 4:
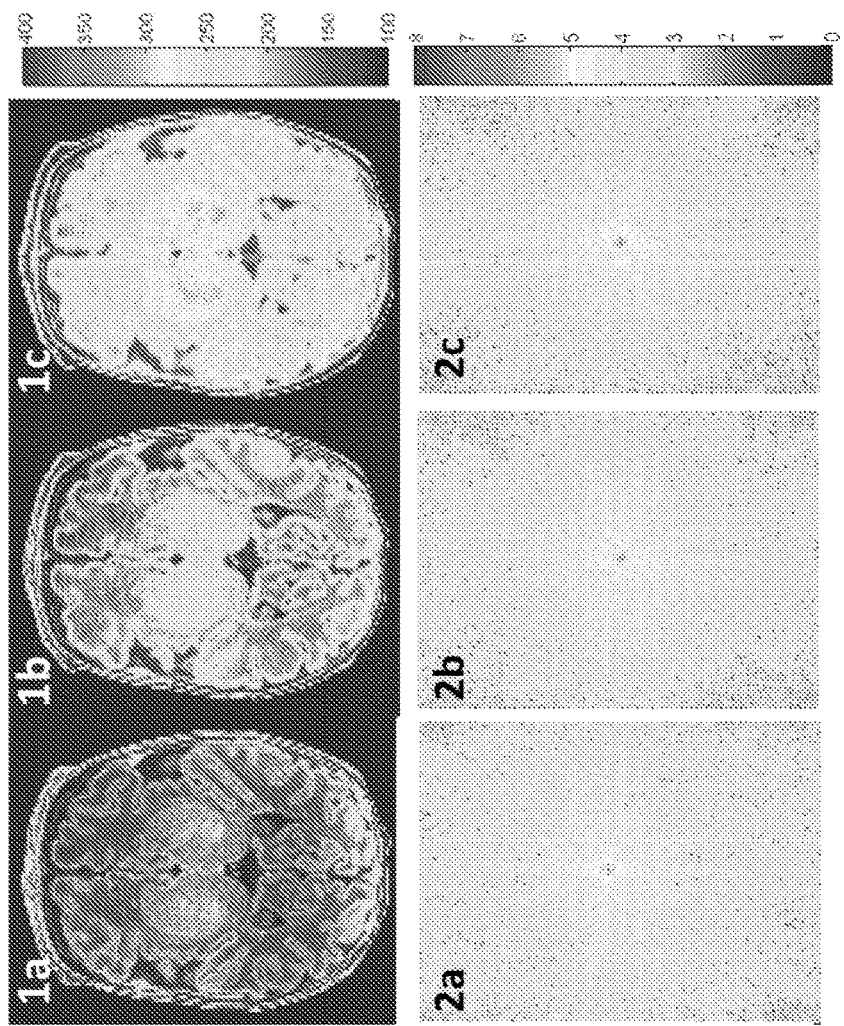
FIG. 4 are in vivo brain images (1a, 1b, and 1c in FIG. 4) with corresponding k-space magnitude data (2a, 2b, and 2c in FIG. 4) of a preterm infant acquired with identical optimized imaging parameters but different acquisition train lengths (ATL): 120 (a), 105 (b), and 90 (c). The signal intensity of the image acquired with an ATL of 90 (i.e., image 1c) is the highest. The magnitude of low spatial-frequency components (near the center) is lowest in k-space magnitude data 2a and highest in k-space magnitude data 2c. Conversely, the magnitude of high spatial-frequency components (edges) is the highest in k-space magnitude data 2a and lowest in k-space magnitude data 2c.

In order to demonstrate the effect of ATL using in vivo brain images, four preterm infants were scanned with identical optimized imaging parameters as proposed above but with different ATLs (i.e. with different slice partial Fourier factors). FIG. 4 illustrates brain images and the corresponding k-space magnitude data of a preterm infant brain acquired at different ATLs. Qualitatively, signal intensity and contrast increased with decreasing ATL. By transforming data from the image domain to the k-space domain, the effect of ATL on k-space spectrum was investigated. Visually, the magnitude of low spatial frequency components (near/at the center) was lowest with an ATL of 120 (k-space magnitude data 2a in FIG. 4), and highest with an ATL of 90 (k-space magnitude data 2c in FIG. 4); conversely, the magnitude of high spatial-frequency components (near the four corners) was highest with an ATL of 120 (k-space magnitude data 2a in FIG. 4), and lowest with an ATL of 90 (k-space magnitude data 2c in FIG. 4).

Figure 5:
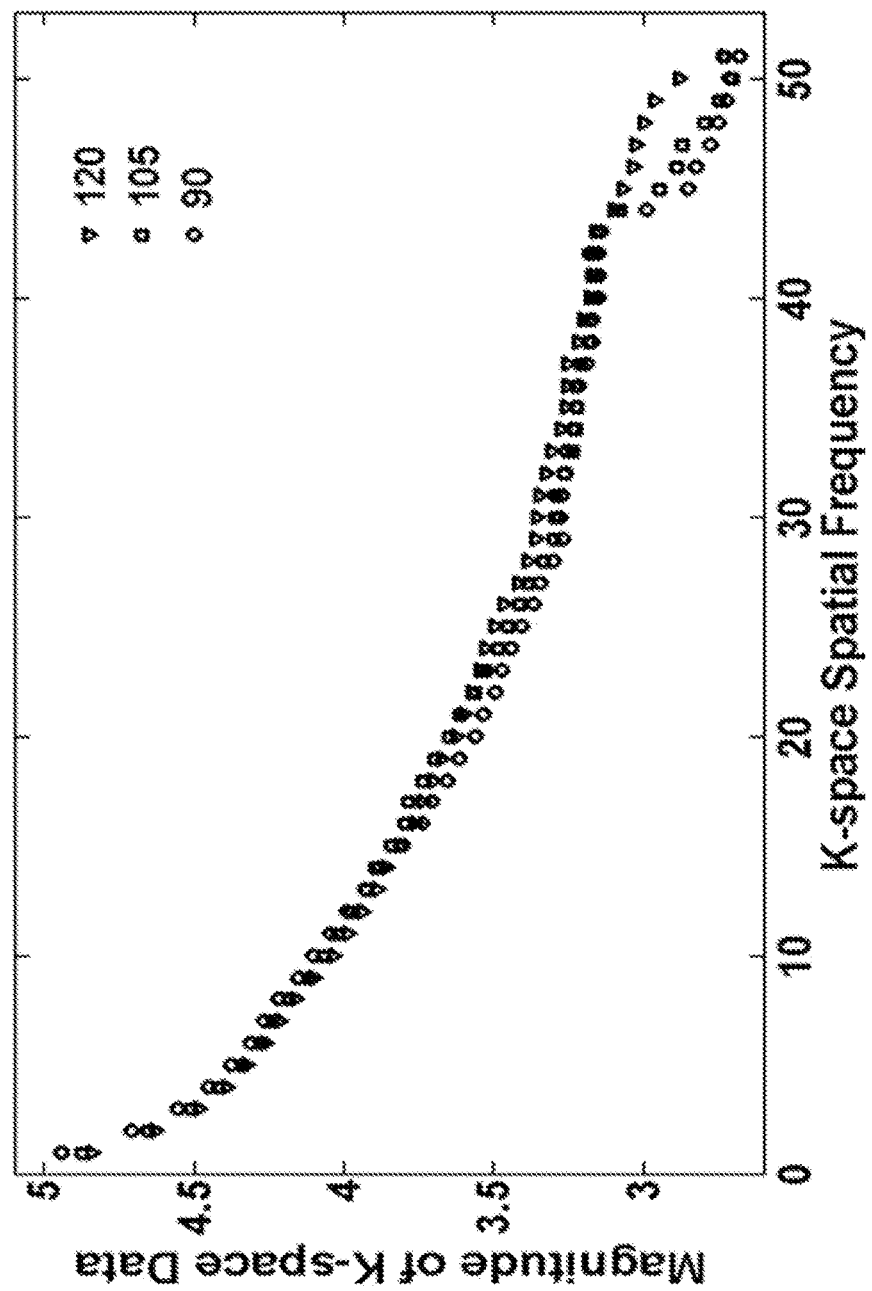
FIG. 5 is a graph illustrating the magnitude of k-space data as a function of spatial frequency computed from images acquired with acquisition train length (ATL) of 120, 105 and 90, respectively. Shorter ATLs lead to higher magnitude of low spatial frequency components and lower magnitude of high spatial frequency components.
Figure 6A:
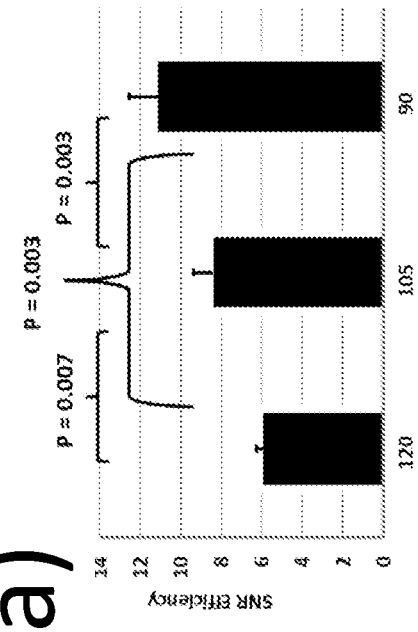
FIGS. 6(a) and 6(b) are graphs illustrating the SNR efficiency (FIG. 6(a)) and CNR efficiency (FIG. 6(b)) from images acquired with acquisition train length (ATL) of 120, 105, and 90, respectively.
Figure 6B:
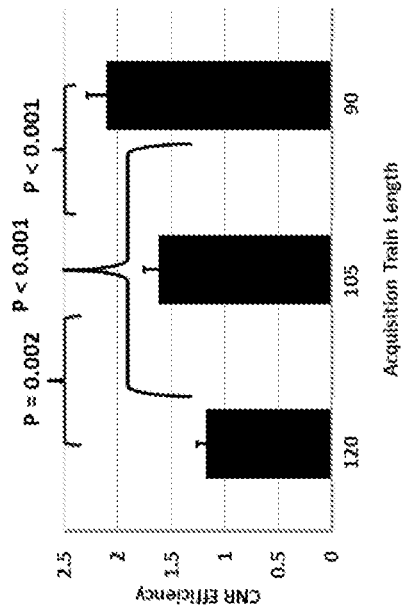

Consistent with FIG. 4, FIG. 5 shows that decreasing ATL improved the magnitude of low spatial frequency components, while reducing the magnitude of high spatial frequency components in k-space. As a result, increased magnitude of low spatial frequency components increased SNR, while decreased magnitude of high spatial frequency components decreased spatial image resolution to a certain extent. Further quantitative analysis suggested that when ATL decreased from 120 to 90, SNR efficiency (e.g., as shown in FIG. 6($a$)) increased on average from 5.9 to 11.1 ($s^{-1/2}$) (by 88%) and CNR efficiency (e.g., as shown in FIG. 6($b$)) improved from 1.18 to 2.11 (by 79%) for these four preterm MP-RAGE images.

FIGS. 8($a$) and 8($b$) are graphs that show the simulated signal intensity of the CSF (FIG. 8($b$)) and GM-WM contrast (FIG. 8($a$)) as a function of the temporal position of the read-out RF pulse at TIs ranging from 200 to 1600 ms with 200 ms increments. The SNR of the CSF is illustrated because the signal intensity of the CSF is the lowest among the major brain tissues (CSF, GM and WM) in T1-weighted images acquired with the MPRAGE sequence. If the SNR of the CSF is acceptable, the SNRs of the GM and WM are also acceptable. As shown in (FIG. 8($a$)), when the temporal position of the read-out RF pulse is more than 30, the signal intensity of the CSF increases monotonically with increasing TI and the temporal position of the readout RF pulse. imax is defined as the temporal position of the read-out RF pulse that corresponds to the maximum GM-WM contrast. As shown in FIG. 8($b$), imax shifts to lower values with increasing TI. imax is not equal to half of the total number of the readout RF pulses. Considering the trade-offs among CSF signal intensity, GM-WM contrast, and hardware limitations, the optimal k-space strategy for neonatal brain imaging on the SIEMENS 3T SKYRA scanner of SIEMENS AG of MUNICH, GERMANY was with slice partial Fourier of 6/8.

Figure 10:
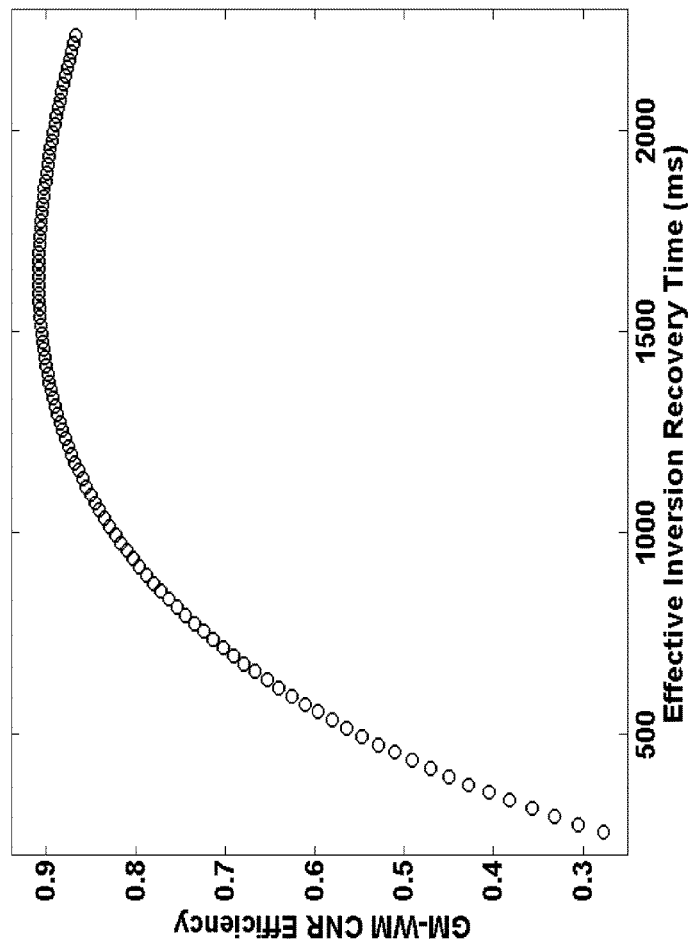
FIG. 10 illustrates simulated contrast efficiency between the gray matter (GM) and white matter (WM) as functions of TI at total 90 read-out RF pulses with a 9.0 ms interval time between readout RF pulses and a flip angle of 13°.
Figure 11:
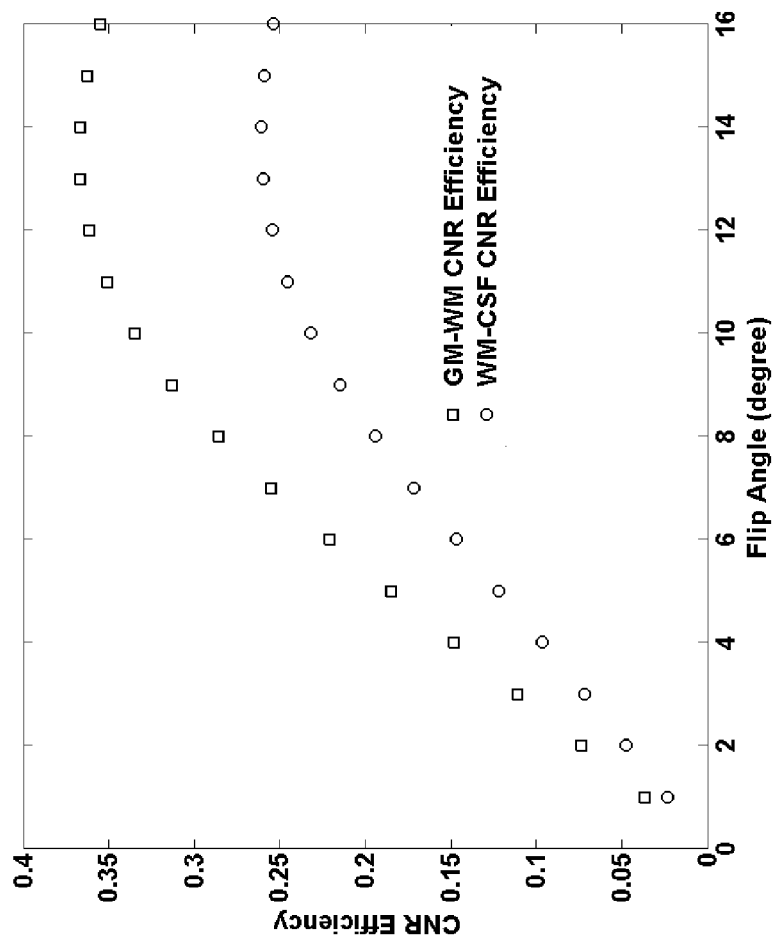
FIG. 11 illustrates simulated gray matter-white matter (GM-WM) CNR efficiency and white matter-cerebrospinal fluid (WM-CSF) CNR efficiency as functions of flip angle for a neonatal brain image acquired with the MPRAGE sequence.

It is well known that effective inversion recovery TIeff is an important imaging parameter for the MPRAGE sequence. According to the optimal k-space strategy, GM-WM CNR efficiency can be used as the objective function to simulate the relationship between CNR efficiency and TIeff (e.g. as shown in FIG. 10). The optimal TIeff is around 1600 ms. Based on the optimal k-space strategy and $TI_{eff}$, both GM-WM and WM-CSF CNR efficiencies can be used as the objective function to obtain the optimal flip angle. The results showed that the CNR efficiencies reached their maximum values at a flip angle of around 13° (e.g., as shown in FIG. 11).

Figure 12:
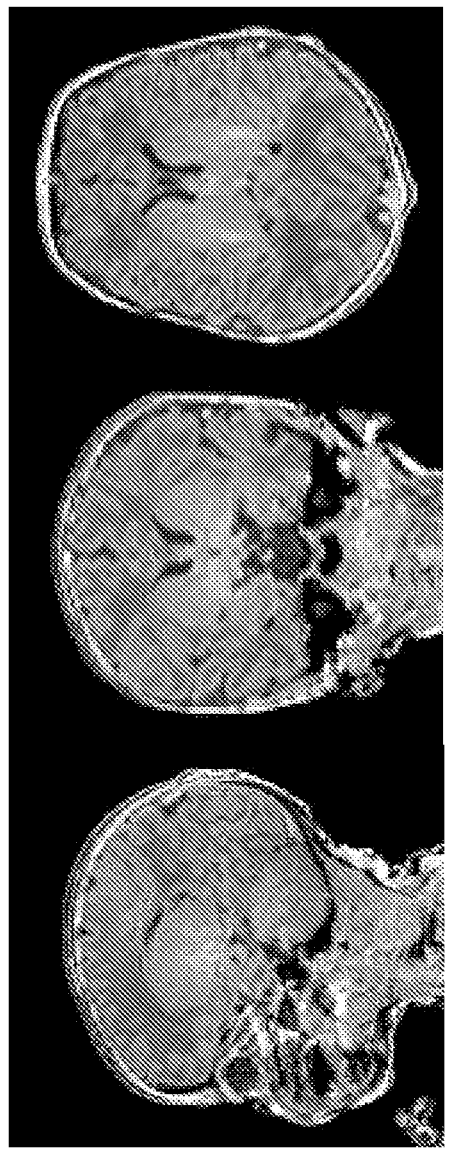
FIG. 12 shows brain images from a healthy full-term neonate acquired using MPRAGE at a flip angle of 13°, an effective inversion recovery time of 1650 ms, a total readout RF pulse of 120, 6/8.

FIG. 12 shows that brain images of a healthy infant acquired using the optimized MRI protocol described herein.

Figure 13:
FIG. 13 shows brain images of a full-term infant with perinatal asphyxia/moderate hypoxic ischemic encephalopathy (HIE) (injury shown by dashed boxes in FIG. 13). The images were acquired using the optimized MRI protocol described herein.

FIG. 13 illustrates brain images of a full-term infant (40 1/7 weeks gestational age) with perinatal asphyxia/moderate hypoxic ischemic encephalopathy (HIE). The infant was born to a 14 year old healthy female after prolonged labor and dystocia (failure to progress). An emergency C-section was performed due to fetal distress. The infant, presented with bradycardia, required positive pressure ventilation with bag-mask for 1 minute, followed by mask CPAP. The Apgar scores were 2, 5, 6 at 1, 5, and 10 minutes, respectively. The birth weight was 3080 g. The infant was diagnosed with neonatal encephalopathy (decreased level of consciousness, decreased activity, low tone, and abnormal reflexes) and transferred to the Nationwide Children's Hospital (NCH) for whole body cooling therapy. After receiving cooling therapy for 3 days, the infant was started on feedings. An MRI exam performed 8 days after birth revealed a relatively large acute/subacute infarct in the left basal ganglia. As this patient is only 8 days old, this could well be related to the prolonged childbirth. The infarctextended inferiorly down the posterior limb internal capsule and into the left pyramidal tract (corticospinal motor tract). MRS did not show a lactate peak. The findings here are believed to be consistent with HIE. The MPRAGE images were comparable in detecting the signal abnormalities to the clinical T1-weighted axial FLAIR images typically used by radiologists to diagnose HIE and offered higher resolution (1 mm versus 3 mm). Because images acquired with MPRAGE are 3 dimensional, the images can be reformatted to obtain three sets of 2D axial, coronal and sagittal images.

Figure 14:
FIG. 14 shows brain images of a late-preterm infant with seizures and severe neonatal encephalopathy (injury shown by dashed boxes in FIG. 14). The images were acquired using the optimized MRI protocol described herein.

FIG. 14 illustrates brain images of a full-term infant with seizures/neonatal enceahalopathy. This infant was also diagnosed with moderate HIE. She was also born at 40 1/7 weeks gestational age to a 19 year old healthy female with good prenatal care. There were signs of fetal distress after failure to progress and vacuum extraction was applied during vaginal birth. The infant was noted to be limp and apneic at birth, and required bag/mask ventilation for 20 minutes followed by CPAP. The Apgar scores were 2, 4, 6 at 1, 5, and 10 minutes, respectively. Her birth weight was 3040 g. The infant was noted to have seizures (bilateral arm stiffening and deviation to right; eye deviation; lip smacking; bicycling movements of lower extremities and tonic/clonic movements of all extremities) soon after birth. She was transferred to NCH for further work-up and treatment. Neuro exam was consistent with encephalopathy (abnormal reflexes such as Moro, suck, and gag, abnormal muscle tone, and weak cry). Based on the presentation, she qualified for cooling therapy (duration: 3 days). Seizures were controlled with phenobarbital therapy.

An MRI exam performed 12 days after birth showed that images demonstrate evidence of symmetric abnormal signal within the thalami, posterior limbs of internal capsules, corpus callosum and cerebral white matter possibly related to HIE. Associated with this, are diminished NAA to creatine ratios for the patient's age. Images acquired with optimized MPRAGE protocol as described herein were used by the radiologist to detect the following: "On the midline sagittal $T_1$-weighted sequence, the body of the corpus callosum appears be thicker than normal measuring approximately 3.6 mm (normal is 2 mm). Corpus callosum is also lower in signal on the $T_1$-weighted images and brighter on the $T_2$-weighted images than expected for this age. Findings suggest edema."

Figure 15A:
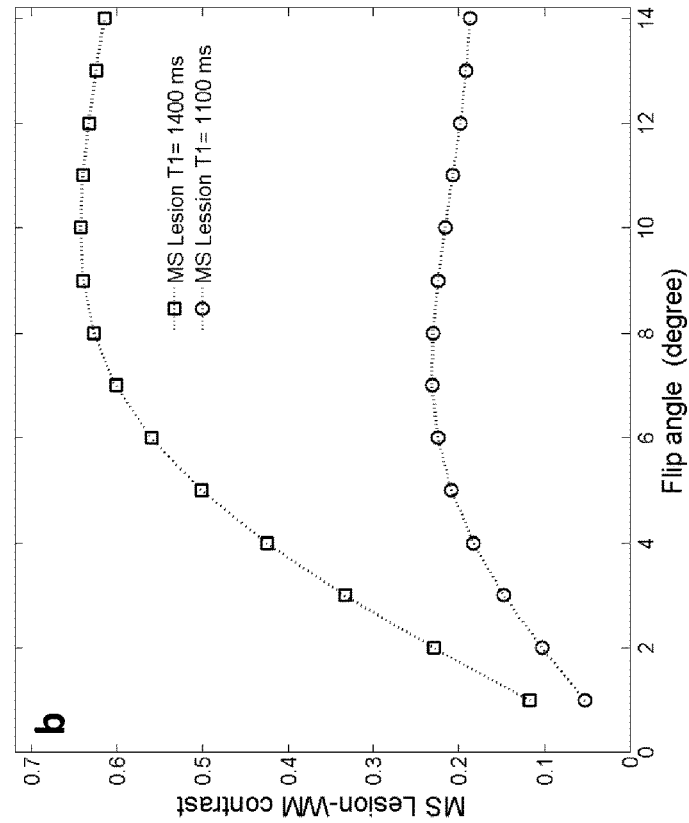
FIGS. 15(a) and 15(b) are graphs illustrating simulated contrast between MS lesion and WM as functions of inversion recover time (TI) (FIG. 15(a)) and flip angle (FIG. 15(b)) at a 10.1 ms interval time between readout RF pulses.
Figure 15B:
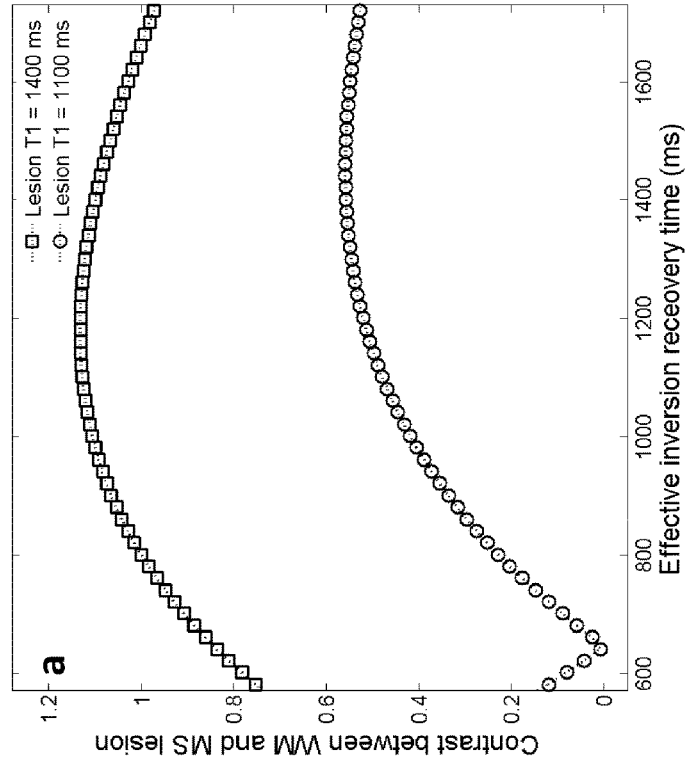

Based on the optimal basic scanner setting and k-space strategy, the contrast between WM and MS lesion (WM-MS contrast) was used as an objective function to simulate the relationship between effective inversion recovery time of MPRAGE acquisition and WM-MS contrast, as shown in FIG. 15(a). It is noted that WM-MS contrast was simulated using both the shortest (1100 ms) and longest (1400 ms) $T_1$ relaxation time of MS lesion, respectively. The results indicated that the optimal effective inversion recovery time was around 1200 ms for the longest MS $T_1$ and 1500 ms for the shortest MS $T_1$. The optimal effective inversion recovery for MS patient is suggested to be the average (around 1350 ms) of the two values. Furthermore, WM-MS contrast was used to optimize the flip angle at the optimal effective inversion recovery time. The optimal flip angle of 8 degree was determined by the simulation results shown in FIG. 15(b).

Figures 16A, 16B:
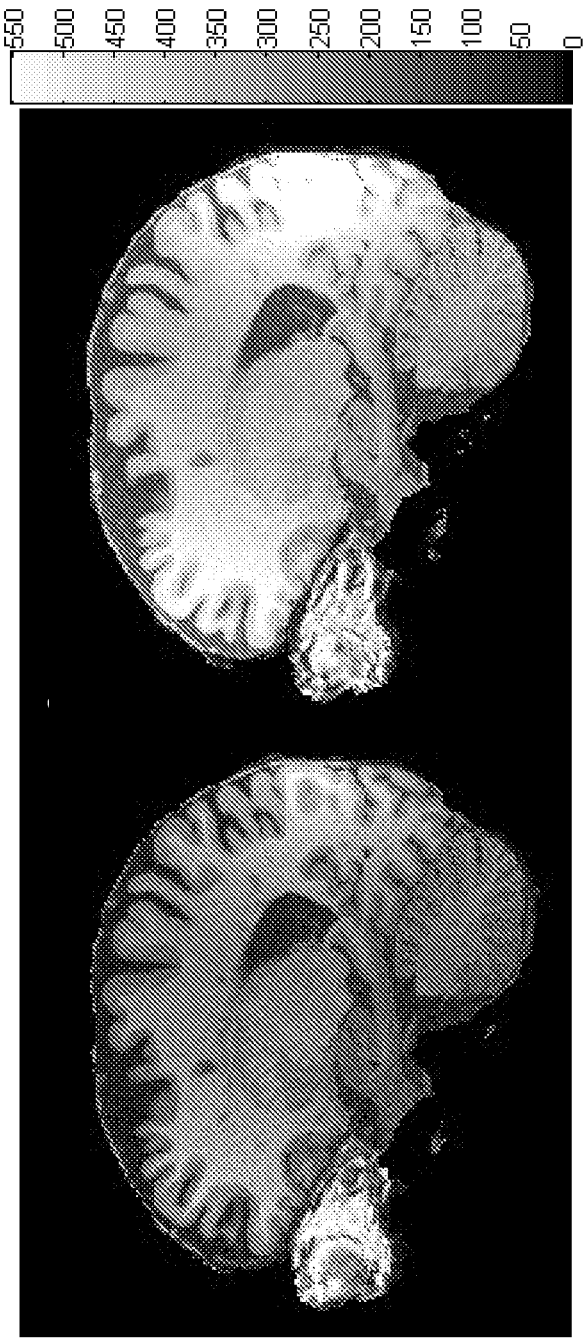
FIGS. 16(a) and 16(b) illustrates brain images of an MS patient acquired with Siemens default protocol (FIG. 16(a)) and the optimized MRI imaging protocol described herein (FIG. 16(b)).

FIG. 16 illustrates brain images of an MS patient acquired with Siemens default protocol (FIG. 16(a)) and the optimized MRI protocol described herein (FIG. 16(b)).

Figure 17:
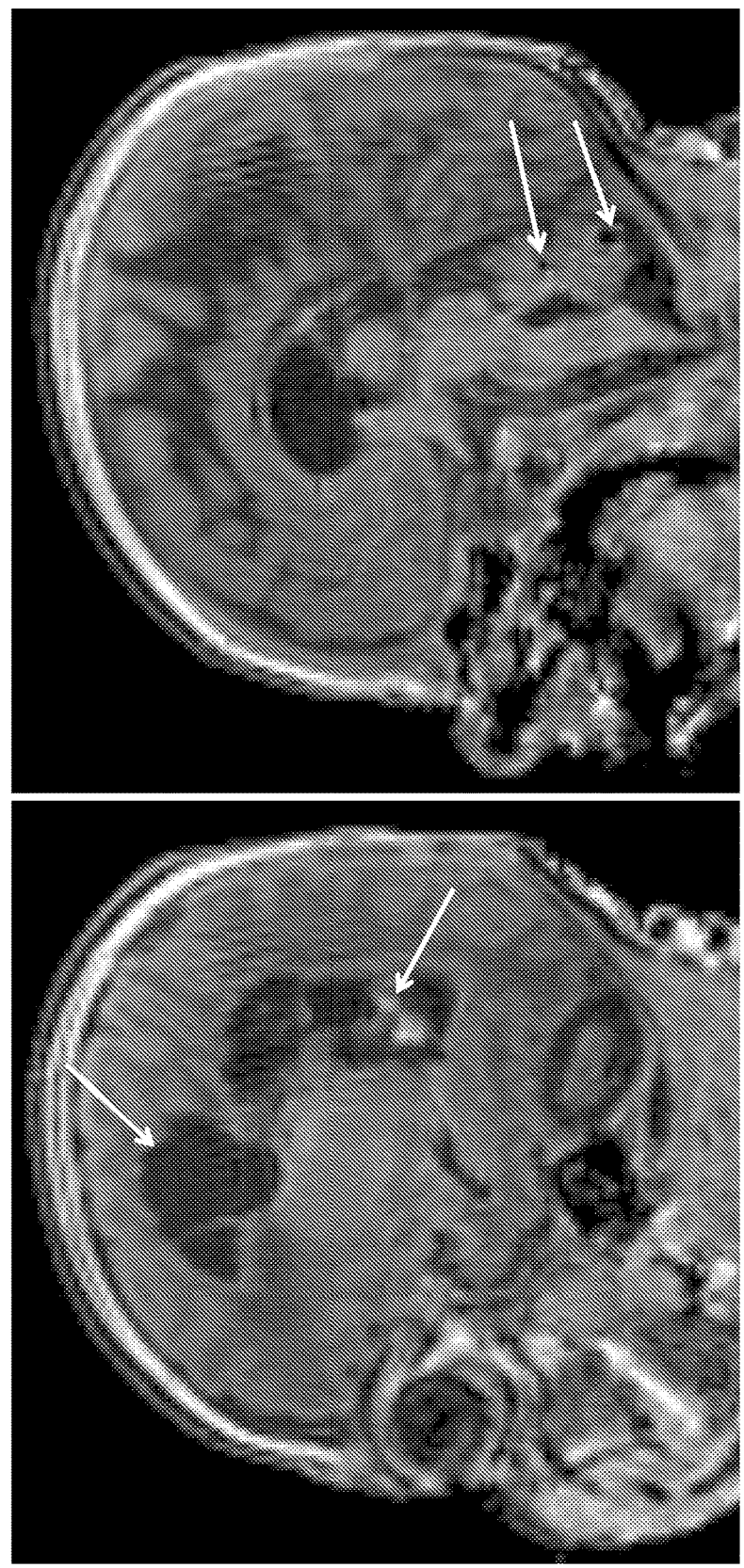
FIG. 17 shows images of a very preterm infant at term with extensive white matter injury/atrophy following germinal matrix-intraventricular hemorrhage and thrombosis of the deep medullary venous systems (shown by arrows in FIG. 17). There is also post-hemorrhagic cerebellar atrophy (shown by arrows in FIG. 17). The images were acquired using the optimized MRI protocol described herein.

FIG. 17 shows images of a very preterm infant at term-equivalent age with PVL and porencephalic changes. In the frontal greater than parietal regions, there is extensive cystic periventricular leukomalacia related to underlying germinal matrix hemorrhages and thrombosis of the deep medullary venous systems. Porencephalic change is present in the right frontal lobe. There is also post-hemorrhagic cerebellar atrophy.

Figure 18:
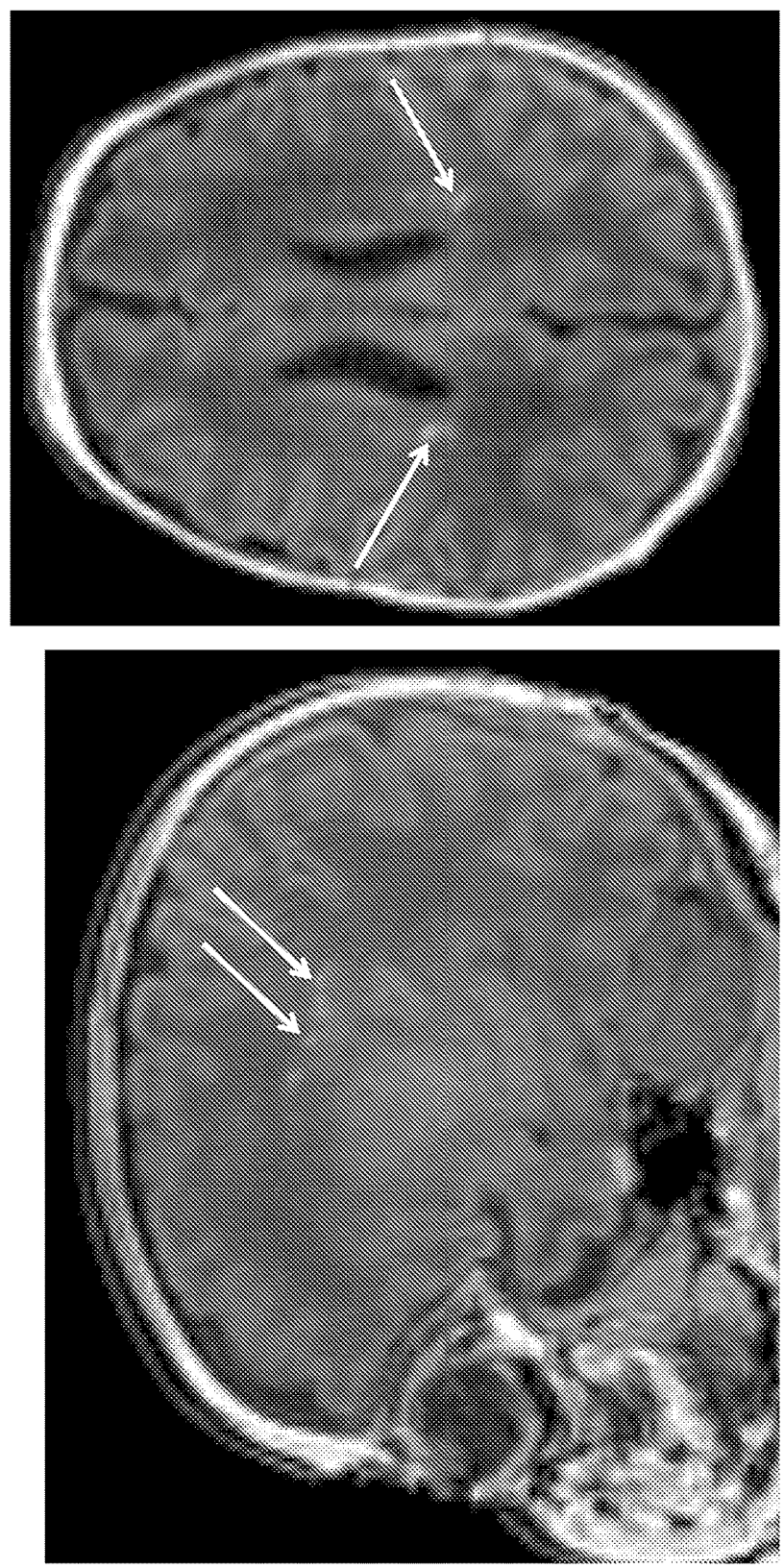
FIG. 18 shows images of a very preterm infant at term-equivalent age (term) with punctate white matter lesions in the periventricular white matter (shown by arrows in FIG. 18). The images were acquired using the optimized MRI protocol described herein.

FIG. 18 shows images of a very preterm infant at term-equivalent age with punctate white matter lesions. Bifrontal and anterior parietal punctate foci of subacute hemorrhage or mineralization within the periventricular white matter suggestive of prior deep medullary venous thrombosis and possible infarction.

FIG. 19 shows images of a very preterm infant at term-equivalent age with hemorrhage with porencephalic changes. 2-3 mm rounded ring like lesion within the right frontal white matter possibly representing old area of injury/hemorrhage.

FIG. 20 shows images of an 8 day old FT infant with moderate scattered subdural and subarachnoid blood likely related to childbirth.

FIG. 21 shows images of an extremely preterm infant imaged at term-equivalent age with the following diseases. Sequela of bilateral germinal matrix hemorrhages with resultant periventricular white matter injury and porencephalic change as well as intraventricular/subarachnoid hemorrhage and posthemorrhagic hydrocephalus. Moderate enlargement of the right lateral ventricle and 3rd ventricle. The 3rd ventricle and right lateral ventricle appear to communicate. A ventriculostomy catheter is in place via a right frontal approach. The appearance is grossly similar to the ultrasound performed Mar. 23, 2015. There is moderate to marked enlargement of the left lateral ventricle, particularly the porencephalic cystic portion in the frontal region. There is compression of the overlying cortical mantle with loss of the sulcal pattern. This implies increased pressure. The left lateral ventricle may not communicate freely with the 3rd ventricle.

Figure 22:
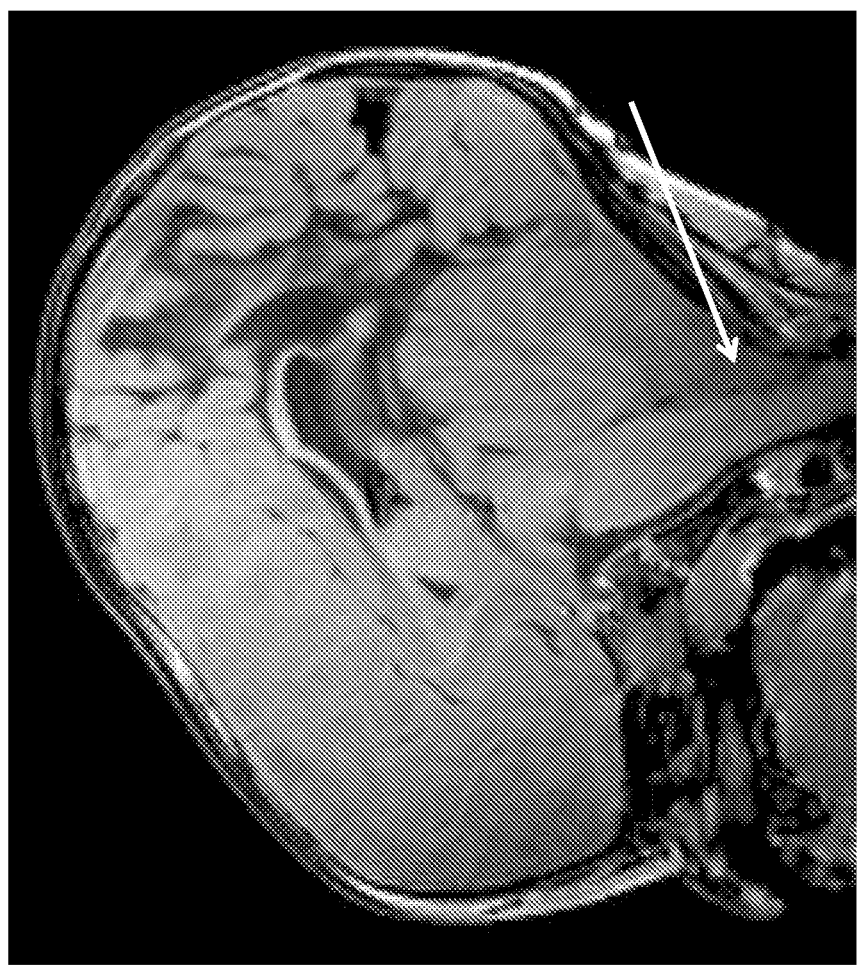
FIG. 22 shows an image of a seven month old infant with prominent Arnold-Chiari II malformation with shunted hydrocephalus (shown by an arrow in FIG. 22). The images were acquired using the optimized MRI protocol described herein.

FIG. 22 shows an image of a 7 month old infant with prominent Arnold-Chiari II malformation with shunted hydrocephalus and interval decrease in lateral and third ventricular size. It is noted that no comparison axial or coronal images are available.

FIG. 23 shows images of a very preterm infant at term-equivalent age with bilateral frontal lobe diffuse excessive high signal intensity (DEHSI) abnormality.

Figure 24:
FIG. 24 shows images of a one year old infant s/p resection of lateral ventricular choroid plexus tumor; significant ventriculomegaly and diffuse brain atrophy is noted in addition to bleeding within the right lateral ventricle (shown by arrows in FIG. 24). The images were acquired using the optimized MRI protocol described herein.

FIG. 24 shows images of a 1 year old infant s/p resection of choroid plexus tumor from lateral ventricle, significant ventriculomegaly, and diffuse brain atrophy along with bleeding into right lateral ventricle.

Figure 25:
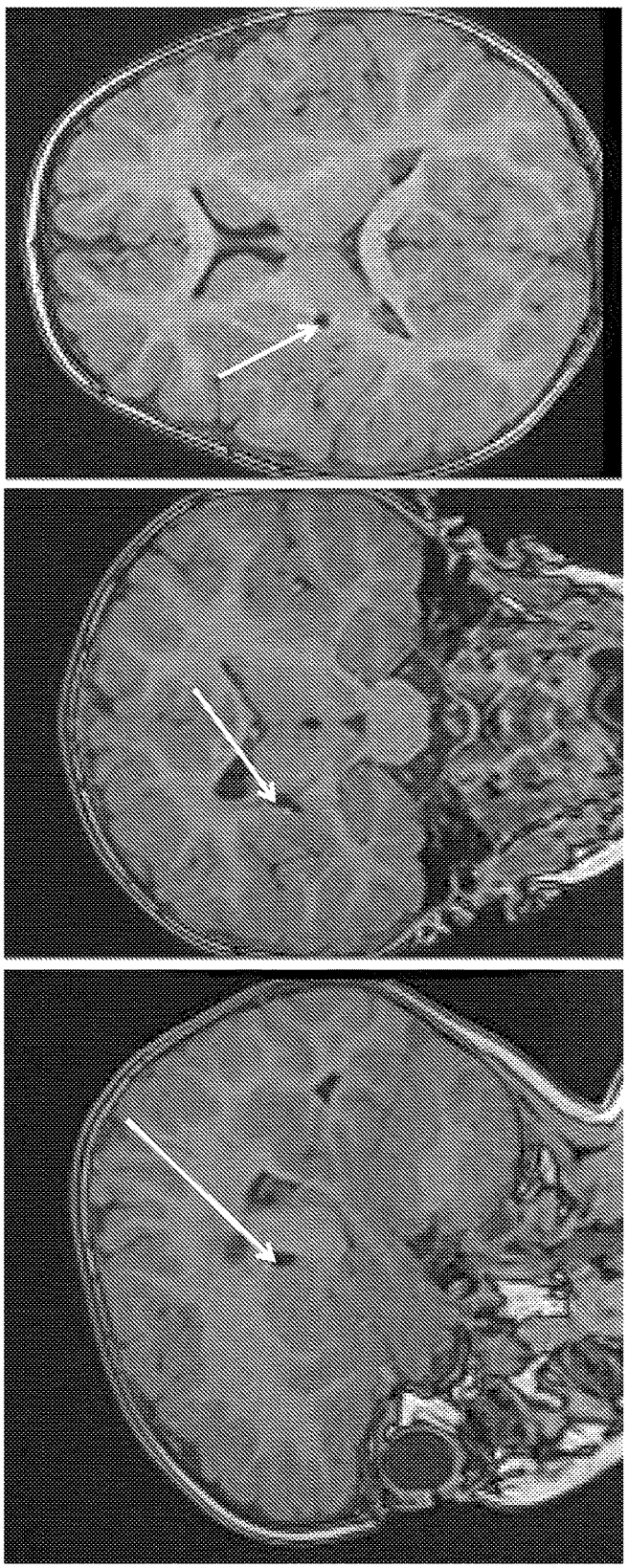
FIG. 25 shows images of a one year old infant with left hemiparesis. Focal area of periventricular leukomalacia is noted in the right posterior limb of the internal capsule (shown by arrows in FIG. 25). The images were acquired using the optimized MRI protocol described herein.

FIG. 25 shows images of a 1 year old who presented with left hemiparesis. Focal area of periventricular leukomalacia is noted in the right posterior limb of the internal capsule.

FIG. 26 shows images of a 8 day old full term infant with relatively large acute/subacute infarct in the left basal ganglia. As this patient is only 8 days old, this could well be related to the prolonged childbirth. The infarct extends inferiorly down the posterior limb internal capsule and into the left pyramidal tract (corticospinal motor tract).

Example Computing Device

When the logical operations described herein are implemented in software, the process may execute on any type of computing architecture or platform. For example, referring to FIG. 27, an example computing device upon which embodiments of the invention may be implemented is illustrated. It should be understood that the computing device 1000 can be incorporated in or remote from an MRI scanner such as the example MRI scanners described above. The computing device 2700 may include a bus or other communication mechanism for communicating information among various components of the computing device 2700. In its most basic configuration, computing device 2700 typically includes at least one processing unit 2706 and system memory 2704. Depending on the exact configuration and type of computing device, system memory 2704 may be volatile (such as random access memory (RAM)), non-volatile (such as read-only memory (ROM), flash memory, etc.), or some combination of the two. This most basic configuration is illustrated in FIG. 27 by dashed line 2702. The processing unit 2706 may be a standard programmable processor that performs arithmetic and logic operations necessary for operation of the computing device 2700.

Computing device 2700 may have additional features/functionality. For example, computing device 2700 may include additional storage such as removable storage 2708 and non-removable storage 2710 including, but not limited to, magnetic or optical disks or tapes. Computing device 2700 may also contain network connection(s) 2716 that allow the device to communicate with other devices. Computing device 2700 may also have input device(s) 2714 such as a keyboard, mouse, touch screen, etc. Output device(s) 2712 such as a display, speakers, printer, etc. may also be included. The additional devices may be connected to the bus in order to facilitate communication of data among the components of the computing device 2700. All these devices are well known in the art and need not be discussed at length here.

The processing unit 2706 may be configured to execute program code encoded in tangible, computer-readable media. Computer-readable media refers to any media that is capable of providing data that causes the computing device 2700 (i.e., a machine) to operate in a particular fashion. Various computer-readable media may be utilized to provide instructions to the processing unit 2706 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 2706 may execute program code stored in the system memory 2704. For example, the bus may carry data to the system memory 2704, from which the processing unit 2706 receives and executes instructions. The data received by the system memory 2704 may optionally be stored on the removable storage 2708 or the non-removable storage 2710 before or after execution by the processing unit 2706.

Computing device 2700 typically includes a variety of computer-readable media. Computer-readable media can be any available media that can be accessed by device 2700 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 2704, removable storage 2708, and non-removable storage 2710 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 2700. Any such computer storage media may be part of computing device 2700.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for optimizing a magnetic resonance imaging (MRI) protocol, comprising:
   receiving one or more MRI scanner settings for an imaging sequence;
   selecting a plurality of objective functions, wherein the objective functions include at least one of a contrast metric, a signal intensity metric, or an artifact metric;
   selecting an acquisition train length;
   selecting a k-space strategy based on the acquisition train length;
   numerically computing respective relationships among the plurality of objective functions and one or more imaging parameters;
   determining one or more optimal imaging parameters based on the numerical computations; and
   acquiring a magnetic resonance (MR) image using the k-space strategy, the acquisition train length, and the optimal one or more imaging parameters.

2. The method of claim 1, wherein selecting a k-space strategy further comprises optimizing k-space strategy.

3. The method of claim 2, wherein k-space strategy optimization is not available for sequences in which each respective k-space acquisition has the same objective function as that used for k-space optimization.

4. The method of claim 2, wherein k-space strategy optimization is available for acquisition train and/or without magnetization preparation.

5. The method of claim 1, wherein the k-space strategy comprises a k-space trajectory and a sampling order.

6. The method of claim 5, wherein the k-space trajectory comprises at least one of a rectilinear, radial, echo planar imaging, spiral, projection reconstruction, random, under-sampled, or partial k-space sampling trajectory, and the sampling order comprises at least one of a sequential, centric, interleaved, reverse, or random sampling order.

7. The method of claim 1, wherein an acquisition train includes at least one of a series of radiofrequency pulses acquisition, refocusing radiofrequency pulse acquisition, and bipolar gradient acquisition.

8. The method of claim 1, wherein MRI scanner settings comprise at least one of receiver bandwidth, parallel imaging techniques, partial Fourier, transmit bandwidth, navigation, trigger options, multi-nuclear options, or saturation band.

9. The method of claim 1, wherein the one or more imaging parameters comprise at least one of a repetition time (TR), echo time (TE), flip angle, refocusing flip angle, magnetization preparation pulses, fat saturation pulses, inversion times, bandwidth, echo train length, echo space time or readout RF number.

10. The method of claim 1, wherein the imaging sequence comprises at least one of two spatial dimensional, three spatial dimensional, or three spatial dimensional plus temporal image acquisition.

11. The method of claim 1, wherein the imaging sequence comprises at least one of a gradient echo, echo planar or spin echo sequence with or without magnetization preparation, with or without under-sampling techniques, with or without parallel imaging techniques, or with or without Cartesian k-space trajectories.

12. The method of claim 1, wherein the acquired image comprises at least one of a magnitude image, a phase image, a real image, an imaginary image, or a complex image.

13. The method of claim 1, wherein the acquired image comprises at least one of an image of a fetus, preterm newborn, full-term newborn, neonate, infant, child, adult, or aging subject with and without disease in a region of interest.

14. The method of claim 13, wherein the region of interest comprises at least a portion of a subject's body with or without disease.

15. The method of claim 14, wherein the portion of the subject's body comprises at least one of any extremity, brain, spine, neck, chest, breast, joint, muscle, prostate, pelvis, or abdomen.

16. The method of claim 13, wherein the disease for the fetus or placenta comprises one or more of tumor, suspected cancer, white matter injury, congenital brain abnormalities, vascular malformations, monochorionic twin pregnancy complications, neural tube defects, caudal regression syndrome, vertebral anomalies, facial clefts, congenital diaphragmatic hernia, congenital pulmonary airway malformation, congenital heart malformation, brain hemorrhage, ventriculomegaly, hydrocephalus, congenital stroke, congenital infections, traumatic brain injury, or suspected drug effects.

17. The method of claim 13, wherein the disease for the preterm and full-term newborn or infant subject comprises one or more of tumor, white matter injury, subcortical gray matter injury, cortical brain injury, hypoxic-ischemic encephalopathy, congenital/perinatal/neonatal stroke, ventriculomegaly, hydrocephalus, metabolic disorders, congenital brain abnormalities, encephalopathy of prematurity, delayed brain maturation, punctate white matter lesions, periventricular leukomalacia, diffuse excessive high signal intensity, intraventricular hemorrhage, other brain hemorrhages, multiple punctate lesions, venous thrombosis, infectious disorders, calcifications, congenital diaphragmatic hernia, congenital pulmonary airway malformations, congenital heart malformations, vascular malformations, congenital stroke, meningomyelocele, traumatic brain injury, suspected drug effects, or neonatal seizures.

18. The method of claim 13, wherein the disease for the child subject comprises one or more of tumor, stroke/ischemia, chronic vascular disease, vascular malformations, arterial or venous/dural venous sinus abnormalities, congenital brain abnormalities, congenital or acquired hydrocephalus, metabolic, disorders, trauma, hemorrhage, inflammatory and autoimmune disorders, infectious disorders, endocrine disorders, evaluation of cranial nerves, psychiatric disorders, assessment of iatrogenic sequelae, image guidance for treatment planning, surgery, or interventional, chronic headaches, migraines, peripheral nervous system disorders, congenital heart disease, pulmonary disorders, inflammatory bowel disease, joint disease/injury, or evaluation of poisoning.

19. The method of claim 13, wherein the disease of adult or aging subjects comprises one or more of tumor, multiple sclerosis, Alzheimer diseases, Psychopathy, Parkinson, atrophy, Huntington's disease, Bipolar disorder, or stroke.

20. The method of claim 1, further comprising using the acquired image for diagnosis, prognosis, surrogate endpoint, or therapeutic response.

21. The method of claim 1, further comprising using the acquired image for computer-aided diagnosis.

22. The method of claim 21, wherein the computer-aided diagnosis comprises a quantification of at least one of volumetric, image intensity, or surface of at least a portion of a region of interest, perfusion, blood volume, flow velocity, relaxation time, diffusion coefficient, proton density, or electro-magnetic properties.

23. A method for optimizing k-space strategy, comprising:
receiving one or more MRI scanner settings and an acquisition train length;
determining one or more magnetic resonance (MR) parameters of a region of interest;
selecting a plurality of objective functions, wherein the objective functions include at least one of a contrast metric, a signal intensity metric, or an artifact metric;
using the one or more MR parameters, numerically computing respective relationships among the plurality of objective functions with the acquisition train length and one or more imaging parameters; and
selecting the k-space strategy to optimize at least one of the objective functions based on the numerical computations.

24. The method of claim 23, wherein a region of interest comprises at least a portion of a subject's body with or without disease.

25. The method of claim 24, wherein the portion of the subject's body comprises at least one of an extremity, brain, spine, neck, chest, breast, joint, prostate, pelvis, or abdomen.

26. The method of claim 25, wherein the numerical computations comprises using Bloch's Equations.

27. The method of claim 26, wherein a solution of Bloch's Equations comprises at least one of an analytic solution, a numerical solution, or an approximation solution.

28. The method of claim 23, wherein the one or more MR parameters change based on at the least one of an age, a pathophysiological change, a physiological change, an electrophysiological change, a disease in tissue, an implanted or injected material, or in-take of medicine.

29. The method of claim 23, wherein the one or more MR parameters comprise at least one of $T_1$ relaxation, $T_2$ relaxation, $T_2$ star relaxation, proton density, diffusion, magnetic susceptibility, oxygen/deoxygenated-hemoglobin, or magnetization transfer.

30. A method for optimizing acquisition train length, comprising:
receiving one or more magnetic resonance imaging (MRI) scanner settings for an imaging sequence;
determining one or more magnetic resonance (MR) parameters of a region of interest;
selecting a plurality of objective functions, wherein the objective functions include at least one of a contrast metric, a signal intensity metric, or an artifact metric;
using the one or more MR parameters, numerically computing respective relationships among an acquisition train length and a plurality of objective functions for the region of interest and one or more imaging parameters;
optimizing the acquisition train length to maximize at least one of the objective functions for the region of interest; and
selecting one or more optimal imaging parameters based on the numerical computations to achieve the optimal acquisition train length.

31. The method of claim 30, further comprising acquiring a magnetic resonance (MR) image using the one or more imaging parameters.

32. The method of claim 30, wherein selecting one or more optimal imaging parameters further comprises adjusting at least one of a number of acquisition train per repetition time, resolution along a phase encoding direction, partial Fourier acquisition, or k-space under-sampling parameter.

33. A method for optimizing imaging parameters, comprising:
receiving at least one of magnetic resonance imaging (MRI) scanner settings for an imaging sequence, an acquisition train length, or a k-space strategy;
determining one or more magnetic resonance (MR) parameters of a region of interest;
selecting a plurality of objective functions, wherein the objective functions include at least one of a contrast metric, a signal intensity metric, or an artifact metric;
using the one or more MR parameters, numerically computing respective relationships among a plurality of objective functions and one or more imaging parameters; and
selecting optimal imaging parameters associated with an optimal objective function based on the numerical computations.

34. The method of claim 33, further comprising acquiring a magnetic resonance (MR) image using the optimal imaging parameters.

* * * * *

UNITED STATES PATENT AND TRADEMARK OFFICE
CERTIFICATE OF CORRECTION

PATENT NO. : 10,444,311 B2
APPLICATION NO. : 15/557120
DATED : October 15, 2019
INVENTOR(S) : Jinghua Wang et al.

It is certified that error appears in the above-identified patent and that said Letters Patent is hereby corrected as shown below:

In the Claims

Column 29, Line 40 for Claim reference numeral 26, "The method of claim 25, wherein the numerical" should read --The method of claim 23, wherein the numerical--

Signed and Sealed this
Twenty-fourth Day of December, 2019

Andrei Iancu
*Director of the United States Patent and Trademark Office*